US010806896B2

(12) United States Patent
Davies et al.

(10) Patent No.: US 10,806,896 B2
(45) Date of Patent: Oct. 20, 2020

(54) STEERABLE MEDICAL DEVICE HANDLE

(71) Applicant: Baylis Medical Company Inc., Missisauga (CA)

(72) Inventors: Gareth Davies, Toronto (CA); Melanie Thompson, Kingston (CA); Deepthi Gorapalli, Ottawa (CA); Steve Copeland, Barrie (CA); Robert G. Dickie, King (CA); Amy Lefler, Mono (CA); Bogdan Beca, Thornhill (CA)

(73) Assignee: Baylis Medical Company Inc., Mississauga (CA)

( * ) Notice: Subject to any disclaimer, the term of this patent is extended or adjusted under 35 U.S.C. 154(b) by 650 days.

(21) Appl. No.: 14/409,662

(22) PCT Filed: Jun. 18, 2013

(86) PCT No.: PCT/IB2013/055013
§ 371 (c)(1),
(2) Date: Dec. 19, 2014

(87) PCT Pub. No.: WO2013/190475
PCT Pub. Date: Dec. 27, 2013

(65) Prior Publication Data
US 2015/0231366 A1  Aug. 20, 2015

Related U.S. Application Data

(60) Provisional application No. 61/661,664, filed on Jun. 19, 2012.

(51) Int. Cl.
*A61M 25/01* (2006.01)
(52) U.S. Cl.
CPC .... *A61M 25/0136* (2013.01); *A61M 25/0147* (2013.01)

(58) Field of Classification Search
CPC .......... A61M 25/0147; A61M 25/0133; A61M 25/0136
See application file for complete search history.

(56) References Cited

U.S. PATENT DOCUMENTS 4,294,233 A  10/1981  Takahashi
5,364,351 A  11/1994  Heinzelman
(Continued)

FOREIGN PATENT DOCUMENTS

EP  0904797 A2  3/1999
EP  1323448 A2  2/2003
(Continued)

OTHER PUBLICATIONS

Patent Cooperation Treaty, International Search Report and Written Opinion of the International Search Authority for International Application No. PCT/IB2013/055013, dated Jan. 20, 2014.
(Continued)

*Primary Examiner* — Kami A Bosworth
*Assistant Examiner* — Leah J Swanson
(74) *Attorney, Agent, or Firm* — Vincent Man; Samuel Tekie; Glenn Arnold

(57) ABSTRACT

A control system and method are provided for control of a steerable catheter, the catheter including at least two control wires, a distal end of each of the control wires being coupled to the catheter at a distal region thereof, the control system comprising: a housing coupled to the catheter; a slide assembly positioned within the housing and operable to translate linearly therein; a proximal portion of each of the at least two control wires being positioned through the slide assembly; and a control knob rotatably coupled to the housing for linearly translating the slide assembly, thereby
(Continued)

enabling the slide assembly to separately manipulate each of said at least two control wires to effect a change in a deflection of said catheter.

29 Claims, 24 Drawing Sheets

(56) References Cited

U.S. PATENT DOCUMENTS

| | | | |
|---|---|---|---|
| 5,395,329 A | | 3/1995 | Fleischhacker |
| 5,462,527 A | * | 10/1995 | Stevens-Wright ......................... A61B 18/1492 600/585 |
| 5,571,085 A | | 11/1996 | Accisano, III |
| 5,891,088 A | * | 4/1999 | Thompson ........ A61M 25/0136 604/524 |
| 5,938,616 A | | 8/1999 | Eaton et al. |
| 5,944,690 A | | 8/1999 | Falwell et al. |
| 6,059,739 A | | 5/2000 | Baumann |
| 6,245,045 B1 | | 6/2001 | Stratienko |
| 7,497,853 B2 | | 3/2009 | Fischer et al. |
| 7,524,301 B2 | | 4/2009 | Dubois et al. |
| 7,615,044 B2 | | 11/2009 | Scheibe |
| 7,691,095 B2 | | 4/2010 | Bednarek et al. |
| 7,959,601 B2 | | 6/2011 | McDaniel et al. |
| 8,056,207 B2 | | 11/2011 | Honebrink et al. |
| 8,308,659 B2 | | 11/2012 | Scheibe et al. |
| 8,911,397 B2 | | 12/2014 | O'Donnell et al. |
| 9,149,607 B2 | | 10/2015 | Scheibe et al. |
| 9,149,608 B2 | | 10/2015 | O'Donnell et al. |
| 2003/0109861 A1 | | 6/2003 | Shimada |
| 2006/0142694 A1 | | 6/2006 | Bednarek et al. |
| 2006/0142699 A1 | | 6/2006 | Lampropoulos |
| 2006/0184106 A1 | | 8/2006 | McDaniel et al. |
| 2007/0260223 A1 | | 11/2007 | Scheibe et al. |
| 2009/0281524 A1 | | 11/2009 | Scheibe et al. |
| 2010/0004592 A1 | | 1/2010 | Butler |
| 2010/0069834 A1 | | 3/2010 | Schultz |
| 2010/0164137 A1 | | 7/2010 | Selkee |
| 2012/0089125 A1 | | 4/2012 | Scheibe et al. |
| 2012/0109079 A1 | | 5/2012 | Asleson et al. |
| 2013/0165857 A1 | | 6/2013 | O'Donnell et al. |
| 2013/0184642 A1 | | 7/2013 | O'Donnell et al. |

FOREIGN PATENT DOCUMENTS

| | | |
|---|---|---|
| EP | 1050316 B1 | 12/2003 |
| EP | 1607118 A1 | 12/2005 |
| EP | 1676595 A1 | 7/2006 |
| EP | 1897581 A2 | 3/2008 |
| EP | 2116272 A1 | 11/2009 |
| EP | 2204208 A2 | 7/2010 |
| EP | 2438954 A1 | 4/2012 |
| EP | 2018203 B1 | 6/2012 |
| EP | 2465568 A1 | 6/2012 |
| EP | 2116272 B1 | 4/2013 |
| JP | H02-289223 | 11/1990 |
| JP | 2006187606 A | 7/2006 |
| JP | 2010194102 A | 9/2010 |
| WO | 9505116 A1 | 3/1995 |
| WO | 9637252 A1 | 11/1996 |
| WO | 9841275 A1 | 9/1998 |
| WO | 0067834 A1 | 11/2000 |
| WO | 2007136984 A2 | 11/2007 |
| WO | 2013096676 A1 | 6/2013 |
| WO | 2013096694 A1 | 6/2013 |

OTHER PUBLICATIONS

Patent Cooperation Treaty, International Preliminary Report on Patentability, International Application No. PCT/IB2013/055013, dated Dec. 23, 2014.
Japanese Office Action for counterpart Japanese Application No. 2015-517905, dated Aug. 1, 2017.
European Patent Office, Communication pursuant to Rules 161 and 162, for counterpart European Application No. 13752677.8, dated Jan. 27, 2015.
Applicant's Reply to Communication pursuant to Rules 161 and 162 for counterpart European Application No. 13752677.8, dated Jul. 31, 2015.
Related Japanese Application, Office Action, dated Jul. 29, 2017.
Related Japanese Application, Office Action, dated May 8, 2018.
Related Japanese Application, Office Action, dated May 11, 2020.
Related Japanese Application, Office Action, dated Aug. 6, 2019.

* cited by examiner

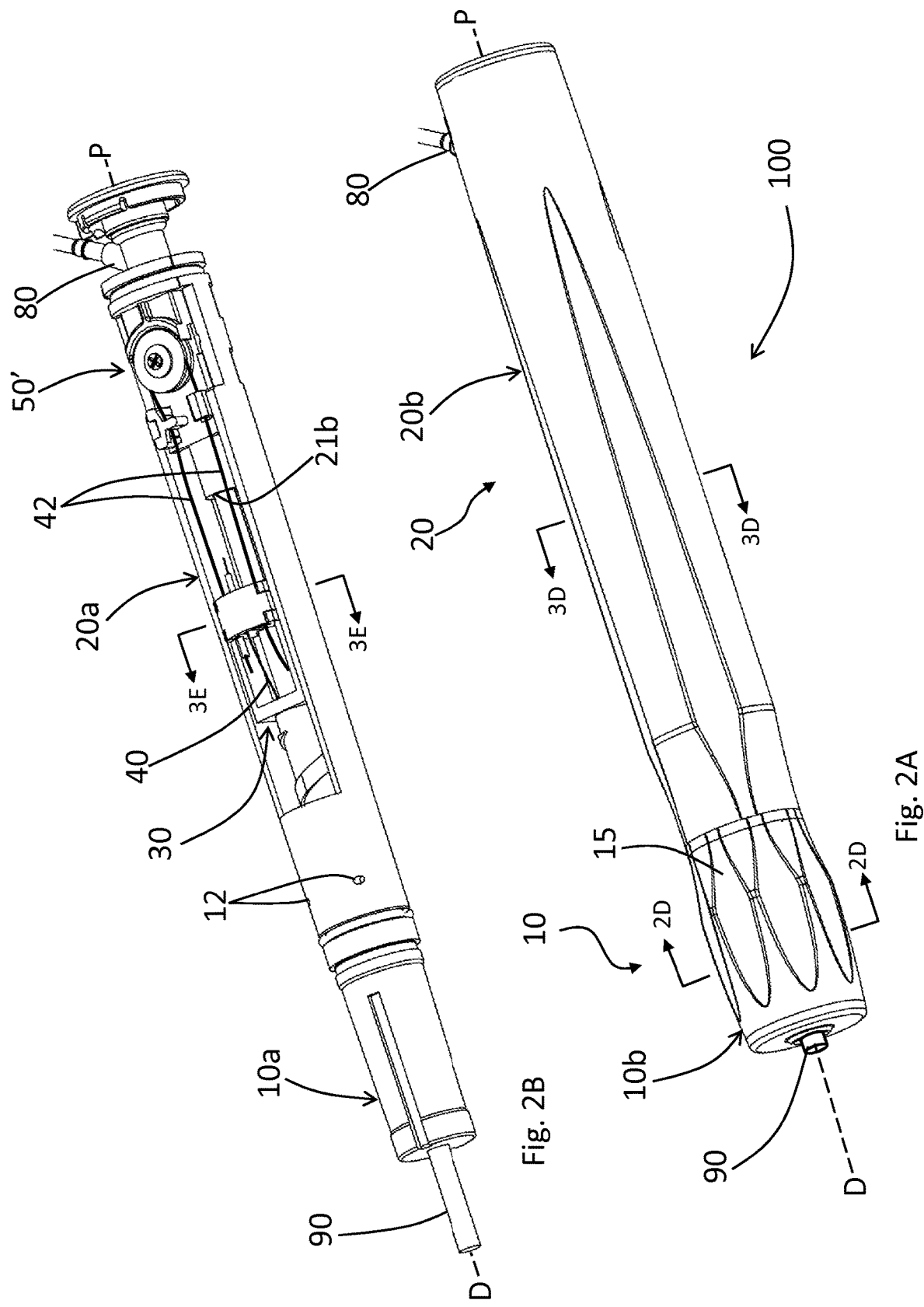

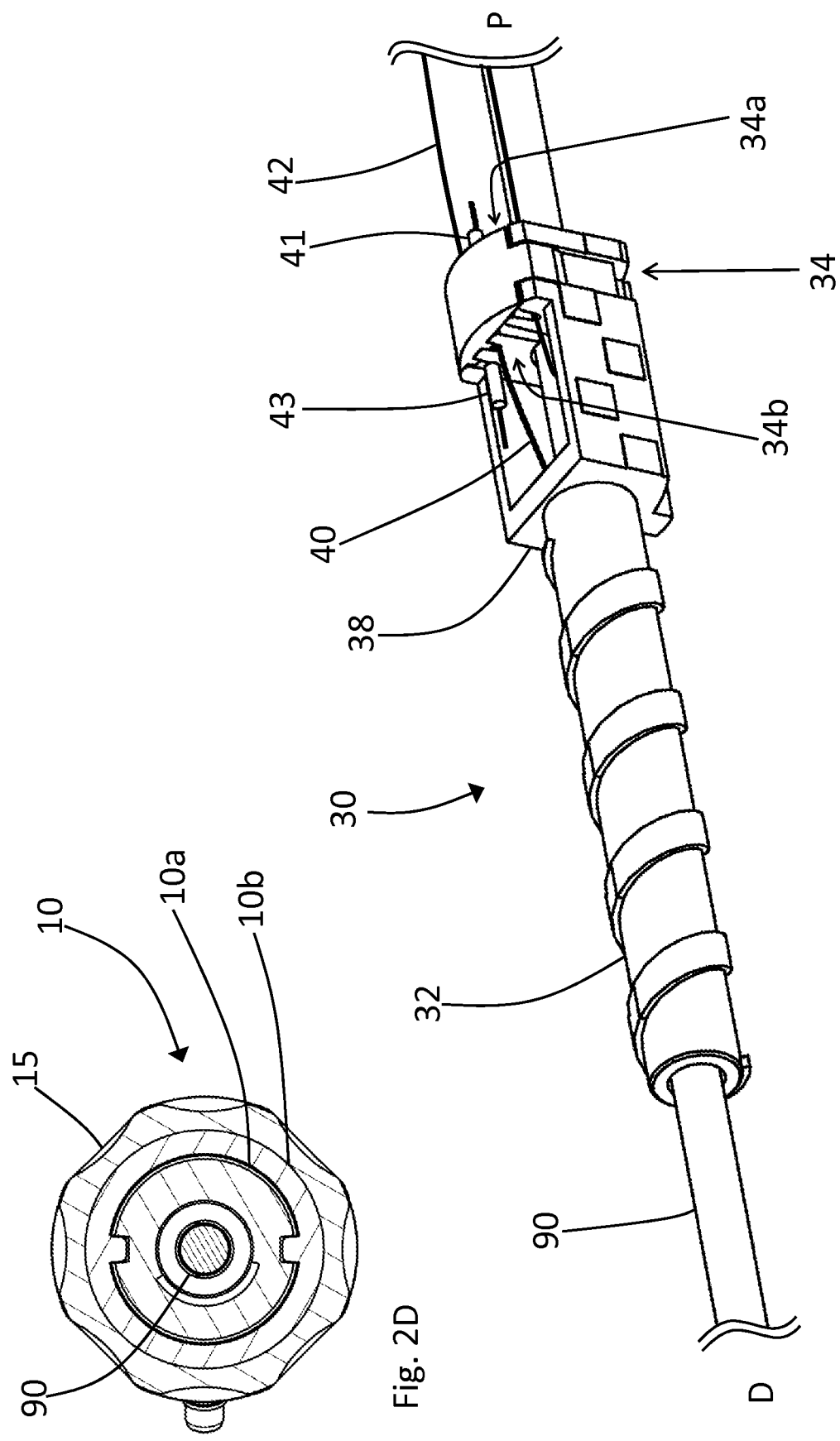

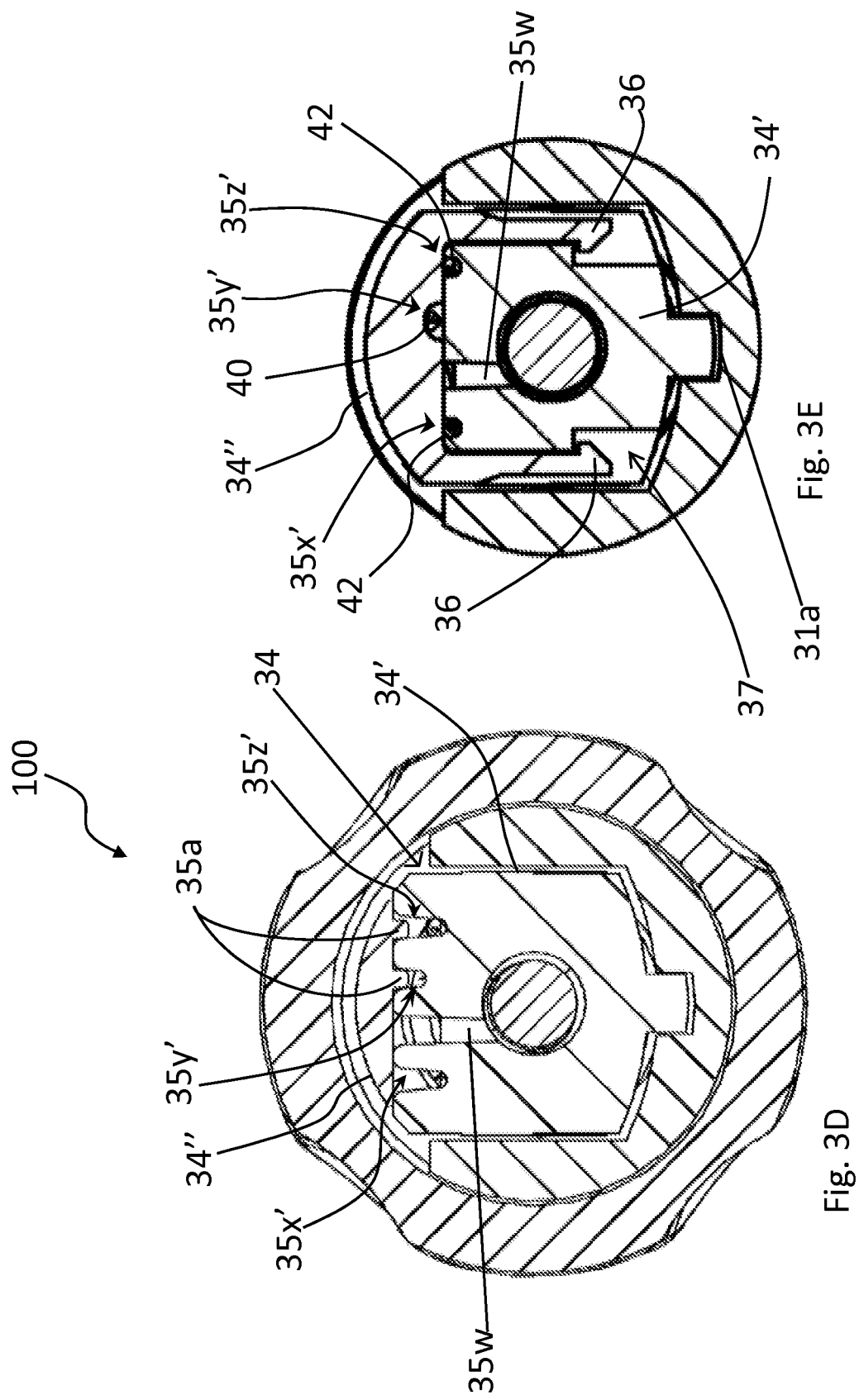

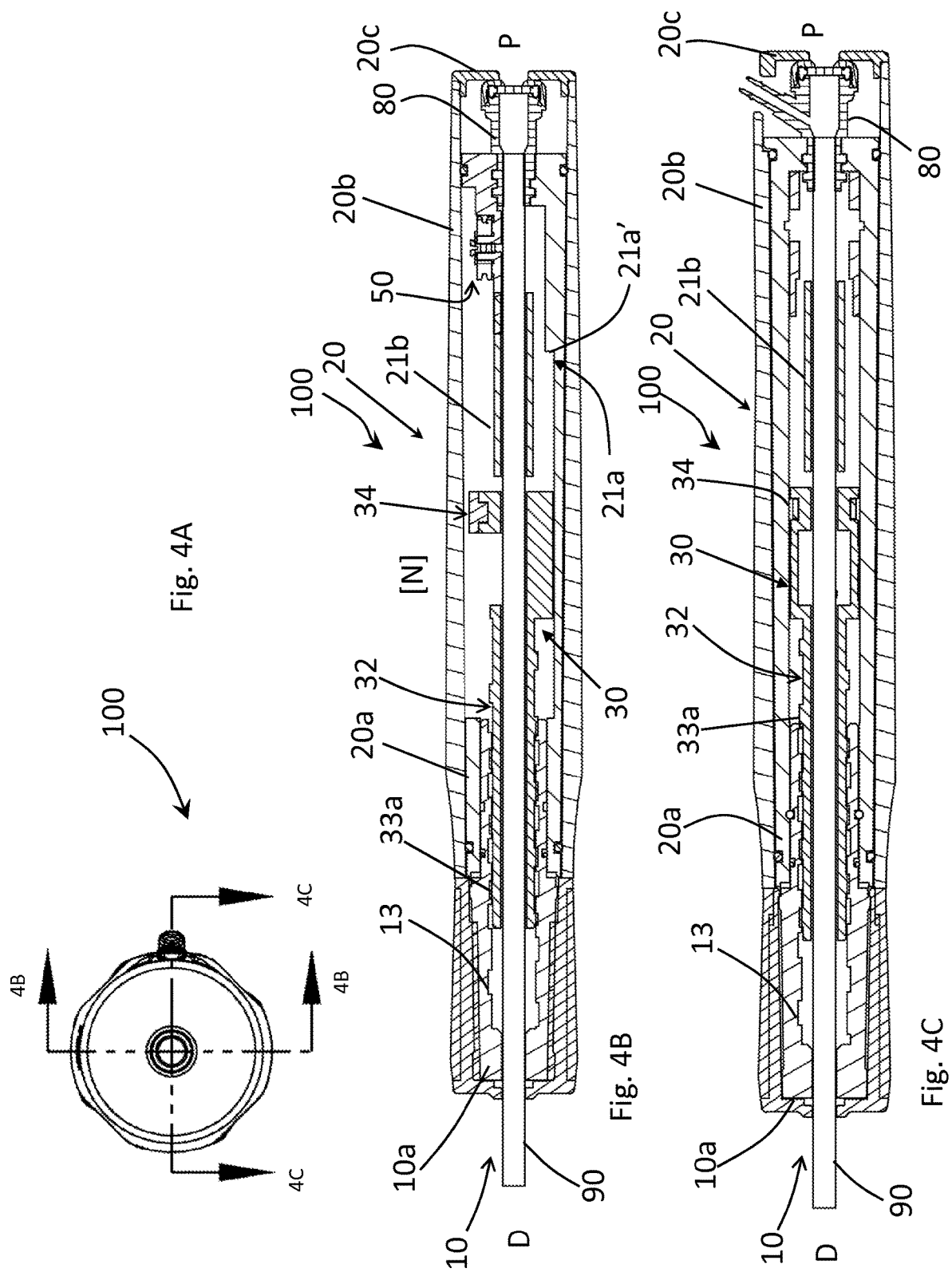

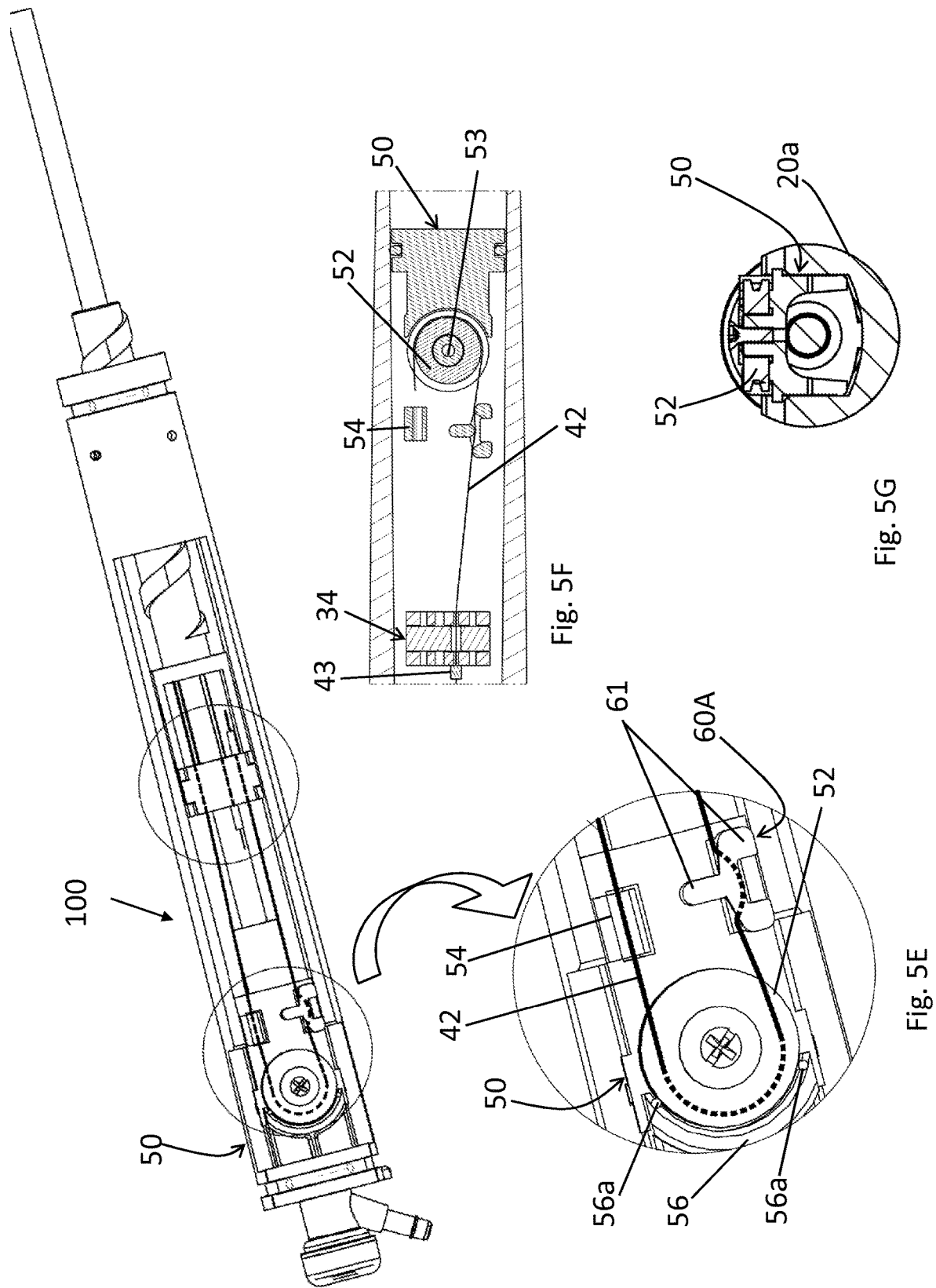

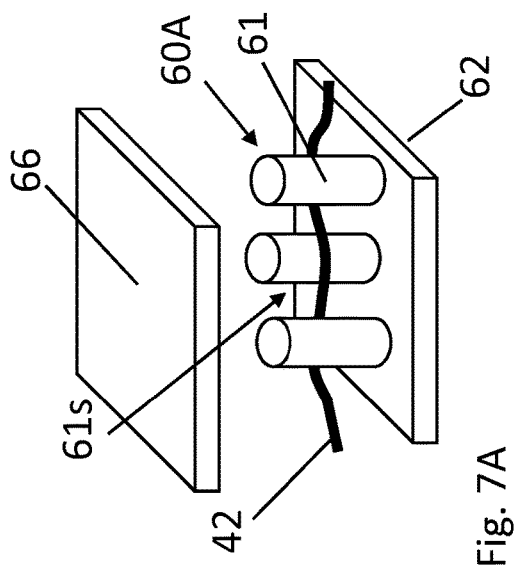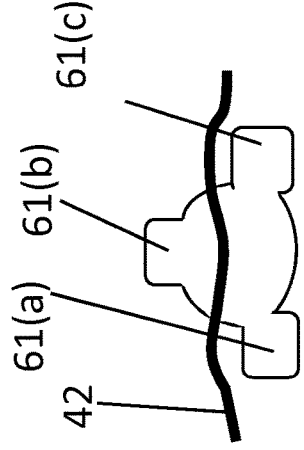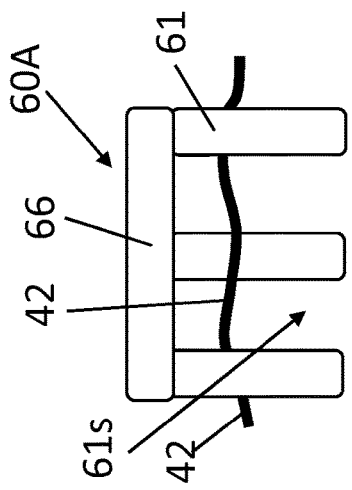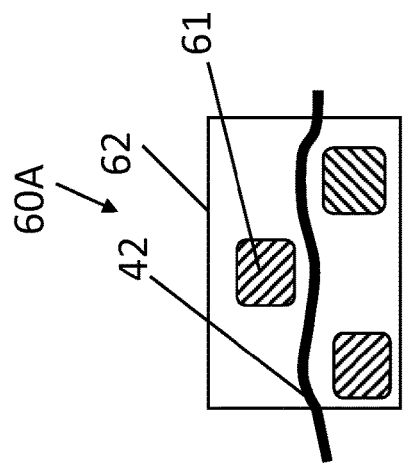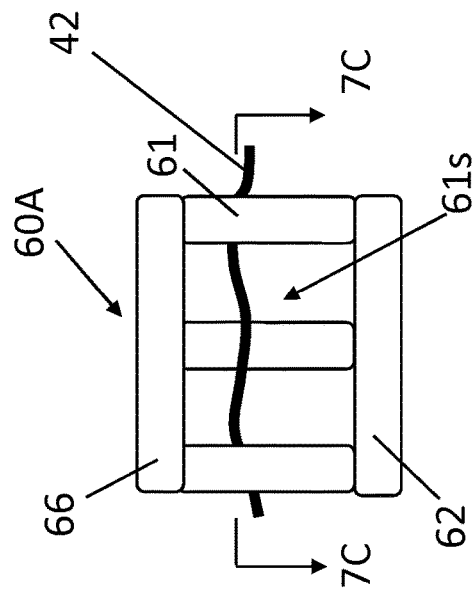

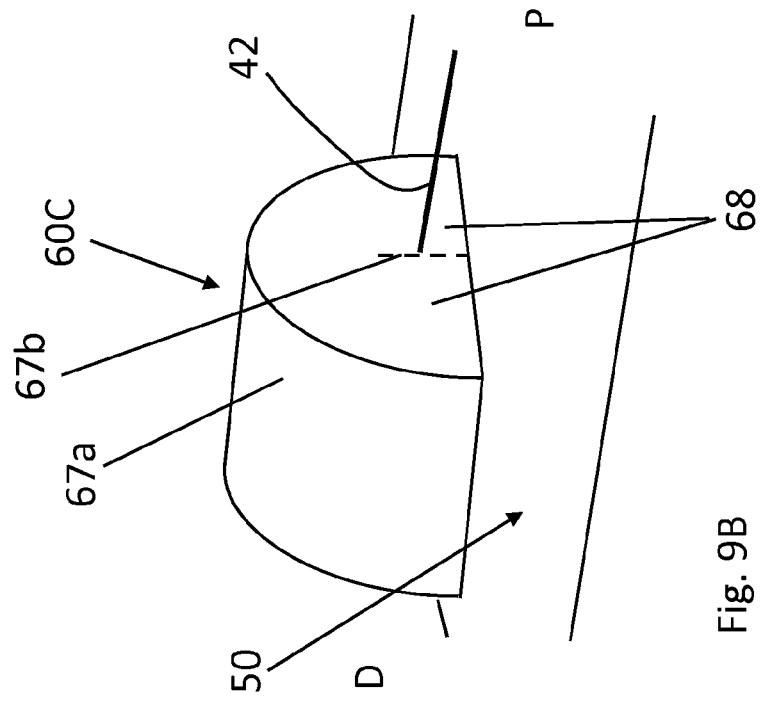
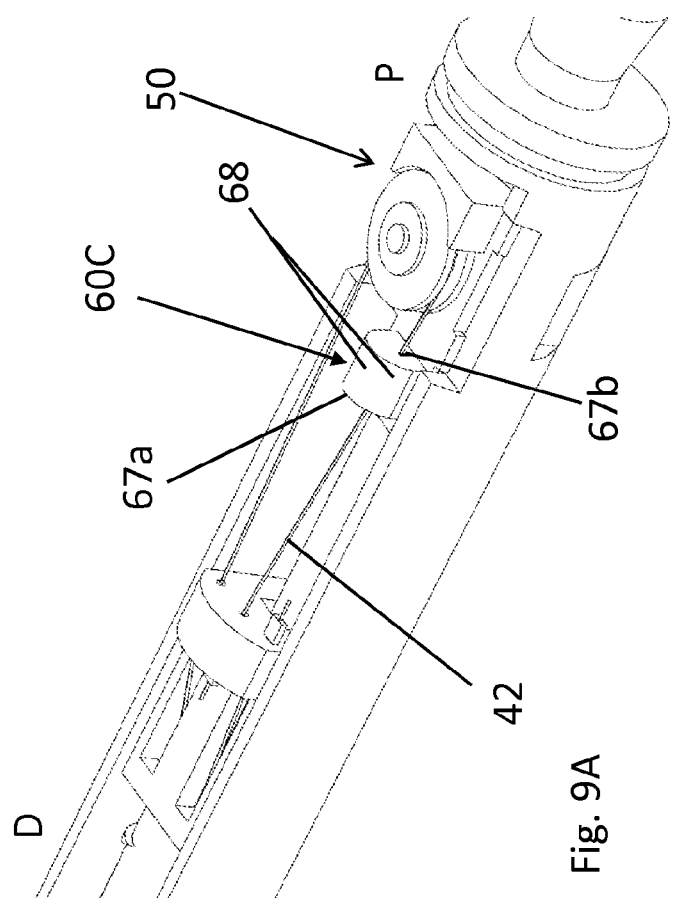
Fig. 9B
Fig. 9A

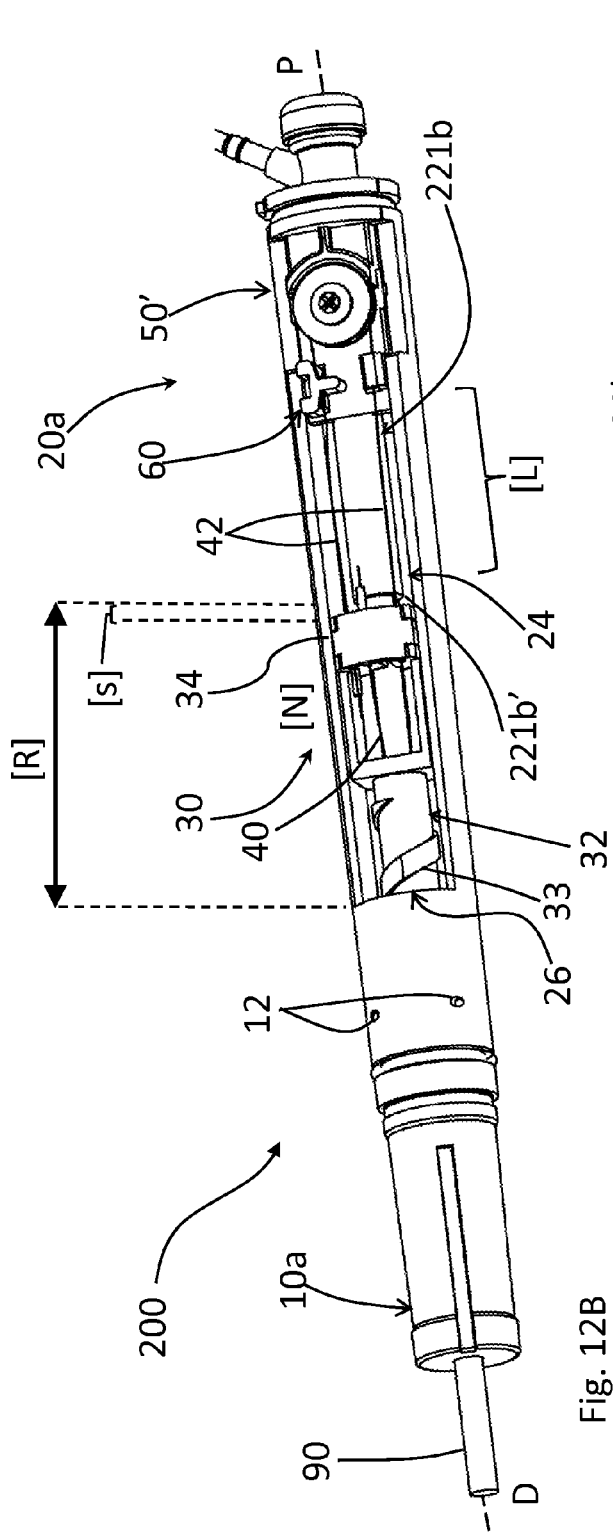
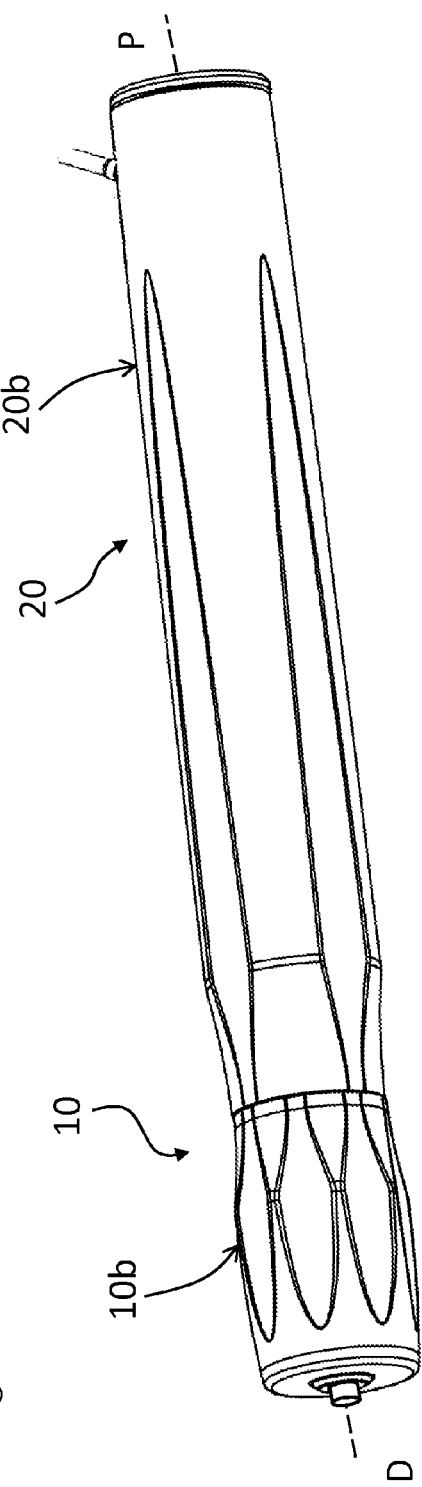
Fig. 12B
Fig. 12A

STEERABLE MEDICAL DEVICE HANDLE

TECHNICAL FIELD

The disclosure relates to a handle for a medical device. More specifically the disclosure relates to a handle for a medical device that enables steering of the medical device in the body.

BACKGROUND OF THE ART

U.S. Pat. No. 5,944,690 granted to Falwell et al. discloses a steerable catheter control mechanism for manipulating a pair of control wires which utilizes a slider mechanism coupled to the proximal ends of the control wires. However, the slider mechanism disclosed by Falwell lacks ease of use as it is awkward to grasp and use. Furthermore, the disclosed slider mechanism provides limited control in steering the catheter. The device provides a thumb control that lacks precision. It is unable to provide precise steering of the catheter as it lacks resolution for permitting minute manipulations needed to provide slight changes in the deflection of the catheter.

U.S. Pat. No. 7,691,095 granted to Bednarek et al. discloses a bi-directional steerable catheter control handle which includes an adjustment knob rotatably connected to the handle. Rotation of the handle results in deflection of two sliding members (each connected to a pull wire) in opposite directions, resulting in respective deflection of the distal end of the catheter. However, the steerable control handle provided by Bednarek is complex and difficult to manufacture.

SUMMARY

In one broad aspect, embodiments of the present invention provide a control system for bi-directional control of a steerable catheter, the catheter including at least two control wires, a distal end of each of the control wires being coupled to the catheter at a distal region thereof, the control system comprising: a housing coupled to the catheter; a slide assembly positioned within the housing and operable to translate linearly therein; a proximal portion of each of the at least two control wires being mounted or positioned through the slide assembly; and a control knob rotatably coupled to the housing for linearly translating the slide assembly, thereby enabling the slide assembly to separately manipulate each of said at least two control wires to effect a change in a deflection of said catheter; wherein rotation of the control knob in a first rotational direction causes the slide assembly to tension one of said at least two control wires by causing distal movement of the slide assembly in a first linear direction to effect a change in the deflection of said catheter in a first deflection direction and wherein rotation of the knob in a second rotational direction causes the slide assembly to tension the other of said at least two control wires by causing proximal movement of the slide assembly in a second linear direction to effect a change in the deflection of said catheter in a second deflection direction.

In another broad aspect, embodiments of the present invention provide a slack limiting device for use with a steerable catheter control system having at least one control wire, the control system comprising a mechanism for tensioning the at least one control wire for deflecting the steerable catheter and for releasing tension there-from, wherein the slack limiting device is engageable with a portion of the at least one control wire for limiting the slack therein when tension is released from the at least one control wire.

In a further broad aspect, embodiments of the present invention provide, a slide limiting mechanism for use with a steerable control system for a steerable catheter having at least one control wire, the steerable control system comprising a handle having a housing with a single slide assembly disposed within the housing that has the at least one control wire coupled thereto, and a rotatable knob for moving the single slide assembly to cause a deflection of the catheter by tensioning the at least one control wire, the slide limiting mechanism comprising:

a slide limiting element positioned within the handle to limit a linear movement of the single slide assembly in a first linear direction within the handle upon rotation of the knob in a first rotational direction, to limit the tension placed on the at least one control wire, for limiting the deflection of the catheter in a first deflection direction.

In an additional broad aspect, embodiments of the present invention provide a method for using a control system to deflect a steerable catheter, the control system comprising a handle having a housing and a single slide assembly disposed within the housing that is operable via a knob, the steerable catheter comprising at least two control wires that are passed through the single slide assembly for engaging therewith, for steering the catheter in opposite deflection directions, the method comprising: moving the single slide assembly in a first linear direction to place one of the at least two control wires in tension by rotating the knob in a first rotational direction, in order to deflect the catheter in a first deflection direction; and moving the single slide assembly in a second linear direction opposite to the first linear direction to place the other of the at least two control wires in tension by rotating the knob in a second rotational direction, in order to deflect the catheter in a second deflection direction.

In still an additional broad aspect, embodiments of the present invention provide a control system for providing unidirectional control of a bi-directional steerable catheter having at least two deflection directions, the control system comprising an actuator for permitting deflection of the bi-directional steerable catheter in a first deflection direction upon actuation in a first direction, and comprising a deflection limiting mechanism for substantially limiting the deflection of the bi-directional steerable catheter in a second deflection direction by limiting actuation in a second direction.

In another broad aspect, embodiments of the present invention provide a slack limiting or containing device for use with a control system for a steerable catheter having at least one control wire, the control system comprising a mechanism for manipulating the at least one control wire for changing a deflection of the steerable catheter, wherein the slack limiting device is engageable with a portion of the at least one control wire for limiting the slack therein during reverse manipulation of the at least one control wire.

BRIEF DESCRIPTION OF THE DRAWINGS

In order that the invention may be readily understood, embodiments of the invention are illustrated by way of examples in the accompanying drawings, in which:

FIGS. 2A and 2B are perspective views showing the external handle assembly and the internal handle assembly, in accordance with an embodiment of the present invention;

FIG. 2D is a transverse cross-sectional view of a steerable handle taken along the line 2D-2D of FIG. 2A, in accordance with an embodiment of the present invention;

FIG. 3A-3B are perspective views of a slide assembly in accordance with an embodiment of the present invention;

FIG. 3D is a transverse cross-sectional view of a steerable handle taken along the line 3D-3D of FIG. 2A, in accordance with an embodiment of the present invention;

FIG. 3E is a transverse cross-sectional view of a steerable handle taken along the line 3E-3E of FIG. 2B, in accordance with an embodiment of the present invention;

FIG. 4A is an end view of a handle assembly in accordance with an embodiment of the present invention;

FIG. 4B is a side cross-sectional view of a handle assembly taken along 4B-4B of FIG. 4A, in accordance with an embodiment of the present invention;

FIG. 4C is a side cross-sectional view of a handle assembly taken along line 4C-4C of FIG. 4A in accordance with an embodiment of the present invention;

FIG. 5E illustrates an enlarged top view of a pulley assembly, in accordance with an embodiment of the present invention;

FIG. 5F is a cross-sectional view of a handle taken along line 5F-5F of FIG. 5A;

FIG. 5G. is a cross-sectional view of a handle taken along the line 5G-5G of FIG. 5B, in accordance with an embodiment of the present invention;

FIG. 6A illustrates a side view of a slack limiting or containing element, in accordance with an embodiment of the present invention;

FIG. 6B illustrates a bottom view of a slack limiting or containing element, in accordance with an embodiment of the present invention;

FIG. 7A-7B are perspective and side views of a slack limiting or containing element, in accordance with an embodiment of the present invention;

FIG. 7C is a sectional view of a slack limiting or containing element along line 7C-7C of FIG. 7B, in accordance with an embodiment of the present invention;

FIG. 9A is a perspective view of handle assembly with an alternate embodiment of a slack limiting or containing element, in accordance with an alternate embodiment of the present invention;

FIG. 9B is a perspective view of a slack limiting or containing element, in accordance with an embodiment of the present invention.

FIGS. 12A-12C illustrate a handle in accordance with alternative embodiments of the present invention.

DETAILED DESCRIPTION

Figure 1:
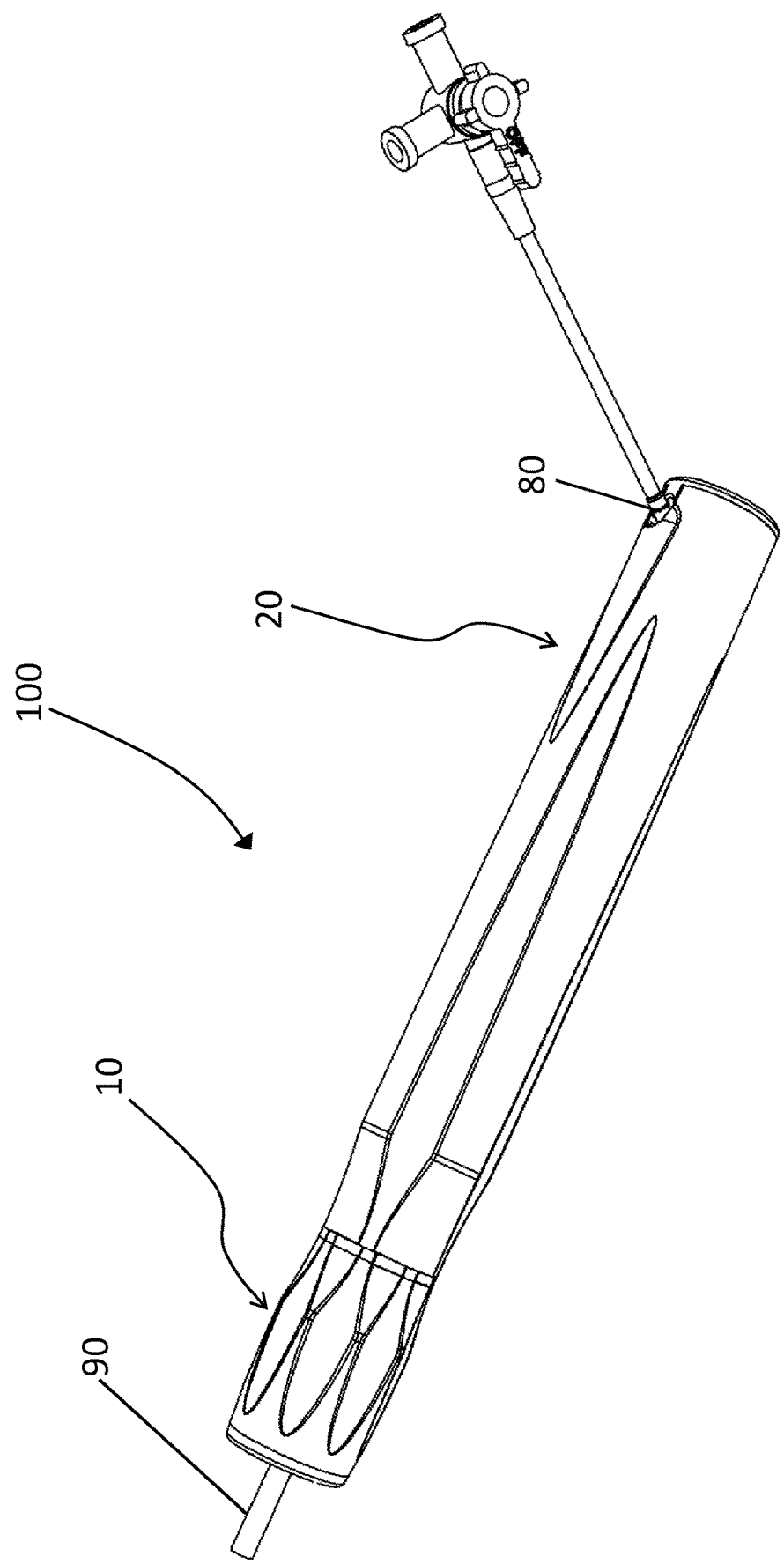
FIG. 1 is a top perspective view of a handle assembly in accordance with an embodiment of the present invention.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As an overview, steerable medical devices have various uses and applications, such as for guiding and positioning devices such as catheters, guidewires and the like within a patient's body. Handles used with such steerable devices typically include a mechanism for actuating one or more pull wires capable of deflecting the steerable device and thus steering or guiding a functional tip of a medical device positioned therein.

While conceiving and reducing the instant invention to practice, the present inventors have discovered a unique design for a bi-directional control system that provides a rotatable control mechanism for operating a slide mechanism of reduced complexity for tensioning two or more control wires to change a deflection of a medical device, such as a steerable catheter apparatus. The rotatable mechanism provides enhanced control of the slide mechanism to enable precise deflections of the medical device while the slide mechanism itself comprised a relatively streamlined design compared to existing products.

As is further described hereinbelow, the present invention provides a rotatable control mechanism such as a handle knob where rotation of the handle knob is converted into a tensioning force exerted separately on each of two control wires via a reduced complexity slide mechanism comprising a single movable slide assembly which is coupled, directly or indirectly, to the control wires. The tensioning force applied to each of the control wires results in a change in deflection of the medical device, such a steerable catheter, to which they are coupled. Embodiments of the present invention thereby avoid the need for having a plurality of sliding members, one for each of the pull wires.

In one broad aspect, embodiments of the present invention provide a rotatable mechanism for controlling deflection of two control wires (also referred to as pull wires) using one moving member to allow a catheter or other medical device to be steered in two different directions. The rotation of the knob in a first rotational direction moves the member along one longitudinal direction to allow one of the two pull wires to be placed in tension (to deflect the catheter to a first orientation) and rotation of the knob in an opposite rotational direction (about a longitudinal axis of the handle) moves the member along the opposite longitudinal direction to allow the other of the two pull wires to be placed in tension (to deflect the catheter to a different orientation).

In accordance with one embodiment, the present invention provides a control system for bi-directional control of a steerable catheter, the catheter including at least two control wires, a distal end of each of the control wires being coupled to the catheter at a distal region thereof, the control system comprising: a housing coupled to the catheter; a slide assembly positioned within the housing and operable to translate linearly therein; a proximal portion of each of the at least two control wires being positioned through the slide assembly; and a control knob rotatably coupled to the housing for linearly translating the slide assembly, thereby enabling the slide assembly to separately manipulate each of said at least two control wires to effect a change in a deflection of said catheter; wherein rotation of the control knob in a first rotational direction causes distal movement of the slide assembly in a first linear direction causing the slide assembly to tension one of said at least two control wires thereby effecting a change in the deflection of said catheter in a first deflection direction and wherein rotation of the knob in a second rotational direction causes proximal movement of the slide assembly in a second linear direction causing the slide assembly to tension the other of said at least two control wires thereby effecting a change in the deflection of said catheter in a second deflection direction.

Overview of the Handle Assembly

In one embodiment of the present invention, a steerable control system or handle 100 is provided for manipulating a medical device. The medical device may include, without limitation, a catheter, sheath, introducer or similar medical devices. In a specific example, as shown in FIGS. 1 and 2A, the handle 100 is coupled to a sheath 90 to enable a user to manipulate or steer the sheath 90 in a desired direction during use. The handle 100 comprises a knob 10 that is rotatably coupled to a handle housing 20. The knob 10 is rotatable about the longitudinal axis of the handle 100 and rotates with respect to housing 20. In operation, the rotation of the knob 10 in a first rotational direction allows the user to steer or deflect the sheath 90 in a first direction, whereas the rotation of the knob 10 in a second rotational direction allows the user to steer or deflect the sheath 90 in a second direction. In some embodiments as described herein, the bi-directional steerable catheter described is operable to be deflected in two different deflection directions, a first and a second deflection direction. In other embodiments, the bi-directional steerable catheter is configured to (or has the internal workings that enable it to) deflect in two different deflection directions; however, the deflection of the catheter in one of its deflection directions is limited or restricted such that the observed deflection of the catheter is limited to a single deflection direction (relative to the starting, or neutral, position). Thus, in some embodiments a unidirectional control system is provided for a bi-directional steerable catheter to provide a unidirectional steerable catheter including at least two control wires.

The rotation of the knob 10 is converted into a deflection of the sheath 90 via a slide assembly 30, shown in FIG. 2B. Generally, knob 10 is co-operatively engaged with the slide assembly 30 which is housed within a lumen defined by the handle housing 20. In a specific example, the knob 10 is threadably engaged with slide assembly 30. The rotation of knob 10 causes a corresponding linear translation of the slide assembly 30 within the housing 20. This translation of the slide assembly 30 is converted into a tensioning of the control wires coupled to the slide assembly 30 and thereby resulting in a deflection of the sheath 90.

More specifically, slide assembly 30 is coupled to respective proximal ends of a pair of control wires that extend substantially along the length of the sheath 90, for example control wires 40 and 42 as shown in FIG. 2B. A distal end (not shown) of each of the control wires 40, 42 is coupled to a distal portion of the sheath 90. The rotation of the knob 10 in one direction causes the slide assembly 30 to translate proximally within the housing 20 pulling one of the control wires (such as control wire 40) to deflect the sheath 90 in a first direction, whereas the rotation of the knob 10 in an opposing direction causes the slide assembly 30 to translate distally within the housing 20 pulling the other of the control wires (such as control wire 42) to deflect the sheath 90 in a second direction.

In one example as shown in FIG. 2B, in order to allow the slide assembly 30 to separately impart a pulling force on each of the two control wires, one of the two control wires (such as control wire 40) is directly coupled to the slide assembly 30 whereas the other of the control wires (such as control wire 42) is indirectly coupled to the slide assembly 30 via a direction reversing element 50' such a pulley or a pin. In other words, a means for of coupling the distal ends of the wires to opposite sides of the slide is included in the handle, whereby motion of the slide in one direction will apply tension to one wire while motion of the slide in the other direction will apply tension to the other wire. As used herein, "directly coupled" is taken to mean that the proximal end of the wire is operably coupled (but not necessarily physically attached or integral with) to the slide without passing through an intermediate structure, while "indirectly coupled" is taken to mean that the proximal end of the wire is operably coupled (but not necessarily physically attached or integral with) to the slide after passing through an intermediate structure or element, such as a direction reversing element.

In a specific example, a proximal end of control wire 40 exits sheath 90 and is routed proximally through the slide assembly 30 to be coupled at or to a proximal face of the slide assembly 30, i.e. proximally of the slide assembly. Thus, in this example, control wire 40 is "directly coupled" to slide assembly 30. Similarly, a proximal end of control wire 42 exits sheath 90 and is routed proximally through the slide assembly 30 where it exits the slide assembly 30. The control wire 42 is then passed around or through the direction reversing element and routed back distally so that it can be passed distally through the slide to be coupled at or to a distal face of the slide assembly 30, i.e. distally of the slide assembly. Thus, in this example, control wire 42 is "indirectly coupled" to the slide assembly 30. As used herein, the distal face of the slide assembly 30 may refer to a distal face of any portion of the slide assembly 30. Similarly, the proximal face of the slide assembly 30 may refer to a proximal face of any portion of the slide assembly 30. As an example, the control wires exit the sheath 90 along a portion of the handle 100 defined by the knob 10 to minimize any excessive angles and/or stress placed on the wire as it is coupled to the slide assembly 30.

Overview of the Knob and Housing

Figure 2C:
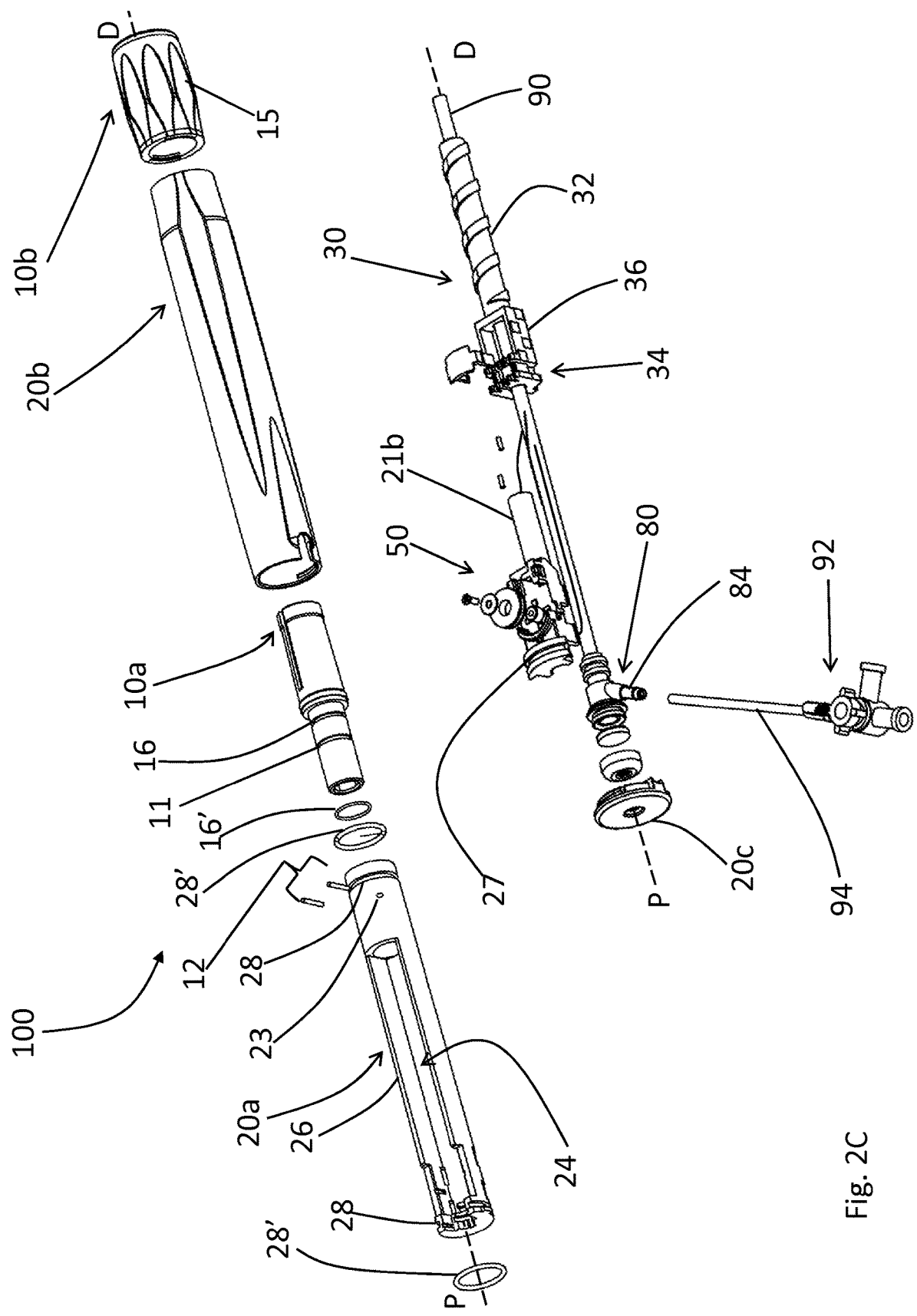
FIG. 2C is an exploded view of a handle assembly, in accordance with an embodiment of the present invention.

As shown in FIG. 2B, the housing 20 comprises an internal housing portion 20a (also referred to as internal housing 20a for conciseness) defining a lumen that is encased by an external or outer housing portion 20b (also referred to as external or outer housing 20b for conciseness). Similarly knob 10 that is coupled to the housing 20, also comprise an inner knob portion 10a (also referred to as inner knob 10a for conciseness) defining a lumen there-through an external or outer knob portion 10b (also referred to as external or outer knob 10b for conciseness) that encases the inner knob 10a. A means is provided to secure the inner knob 10a to the inner housing 20a. In one embodiment a portion of the inner knob is received within the inner housing to allow one or more pins 12 to be inserted transversally through the inner knob 10a and the inner housing 20a to secure them in place. The pins 12 may comprise a metal such as stainless steel. In a specific example, apertures or holes 23 may be provided in the inner housing 20a and a circumferential groove 11 (as shown in FIG. 2C), may be provided in a proximal portion of inner knob 10a, each for receiving the pins 12. The pins 12 lock the inner knob 10a and inner housing 20a together to prevent longitudinal displacement while permitting rotational movement with respect to each other. In other words, the inner knob 10a is free to rotate with respect to inner housing 20a, while maintaining translational coupling/locking of inner knob 10a with the inner housing 20a. In a specific example, the handle 100 comprises two pins 12 that couple the inner knob 10a to the inner housing 20a. In one example, the knob 10 is positioned at the distal end of the handle defining the distal direction (D) and the opposing end of housing 20 forms the proximal end of the handle defining the proximal direction (P), as marked in the drawings. In an alternate example a single aperture or hole 23 may be provided for receiving a pin 12.

In one embodiment, as shown in FIG. 2C, the inner housing 20a defines a lumen 24 there-through for housing the slide assembly 30 and to allow translation of the slide assembly 30 therein. The inner housing 20a further comprises a window 26 which may guide the slide assembly 30 during translation and may also provide access to aid in coupling the control wires 40, 42, to the slide assembly 30. In some embodiments the inner housing 20a additionally comprises a groove or track 21a to guide and limit the translation of the slide assembly 30 (shown in FIG. 4B). In one embodiment, both the inner housing 20a and the outer housing 20b may comprise a polymer. As a particular example, the inner housing 20a comprises Acrylonitrile butadiene styrene (ABS) and the outer housing 20b comprises polypropylene. In other embodiments, the housing 20 may comprise a metal.

In one example, the outer knob 10b comprises inwardly extending projections that co-operatively engage with/fit into grooves within the inner knob 10a. This allows the inner knob 10a to be rotated along with the outer knob 10b. Thus rotational motion of the outer knob 10b is imparted to the inner knob 10a and they can be operated as a single unit. In one embodiment as shown in FIGS. 2B and 2C the inner knob 10a may be tapered towards the distal end. The inner knob 10a and the outer knob 10b may also comprise a polymer. As a particular example, the inner knob 10a comprises DUPONT™ DELRIN® 100P and the outer knob 10b comprises polypropylene.

In some embodiments, the outer knob 10b may have an exterior comfort grip 15 disposed thereon, as shown in FIG. 1-2B. An example of a grip 15 is additionally shown in a cross-sectional view illustrated in FIG. 2D. The comfort grip 15 may comprise an elastomer layer that is over-molded onto a portion of the outer knob 10b. In a particular example, the exterior comfort grip 15 comprises Santoprene® SSA 55 that is over-molded onto a portion of the outer knob 10b that comprises polypropylene.

Overview of Slide Assembly

Figure 3B:
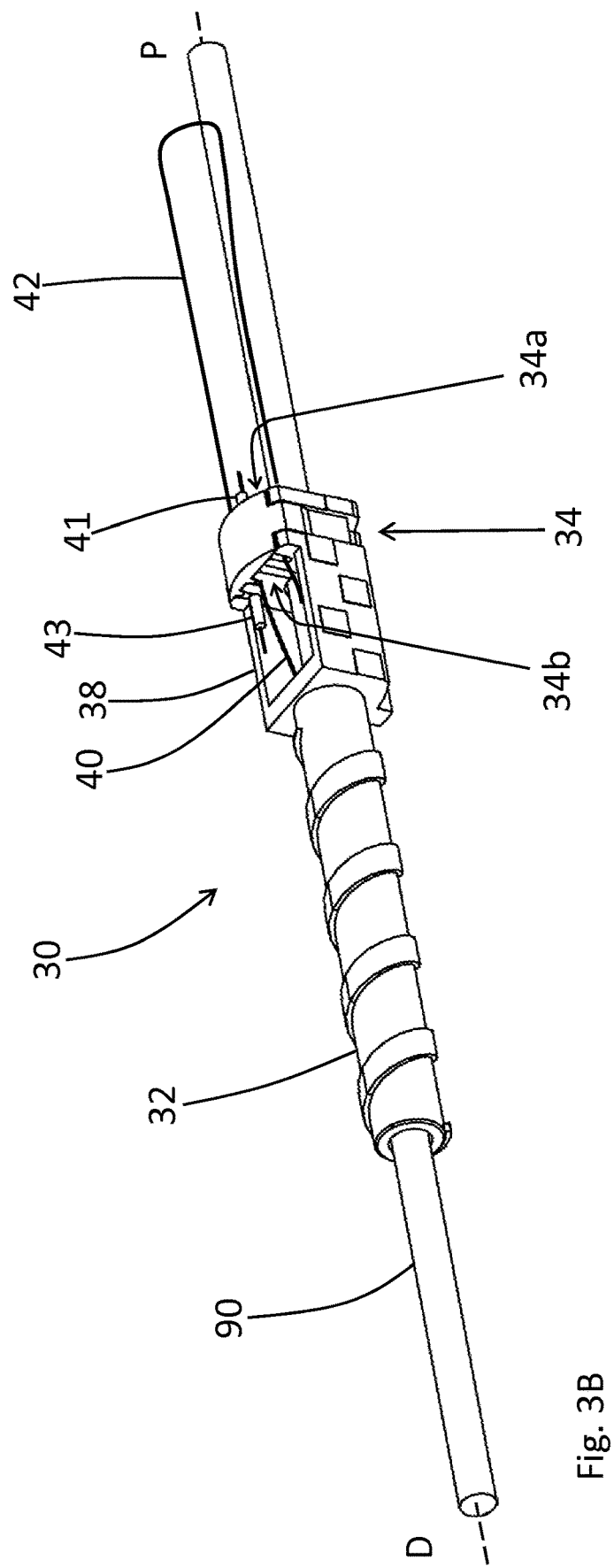

In a specific example as shown in FIG. 3A, the slide assembly 30 comprises a bolt 32 and an intermediate housing 38 comprising a carriage 34. The carriage 34 comprises a carriage proximal face 34a and a carriage distal face 34b. Each of the control wires 40, 42 that exit from sheath 90 pass through the carriage 34 with control wire 40 being operably coupled at or to the proximal face 34a of the carriage 34 using a crimp 41. Crimp 41 substantially abuts against the proximal face 34a and ensures that as the slide assembly 30 translates proximally it pulls the wire 40 along with it. Similarly, the control wire 42 is operably coupled to carriage 34 using a crimp 43. Crimp 43 substantially abuts against the distal face 34b of the carriage 34 and ensures that as the carriage 34 translates distally it pulls control wire 42 along with it. As shown in FIG. 3B control wire 42 is initially routed proximally through the carriage 34 and is then looped around so that it passes distally through the carriage 34 to be coupled to the distal face 34b. In some embodiments the control wires 40, 42 may be pre-crimped. In other embodiments the control wires 40, 42 may be crimped post-assembly after being routed through the slide assembly 30.

Example 1: A Two Part Slide Assembly

Figure 3C:
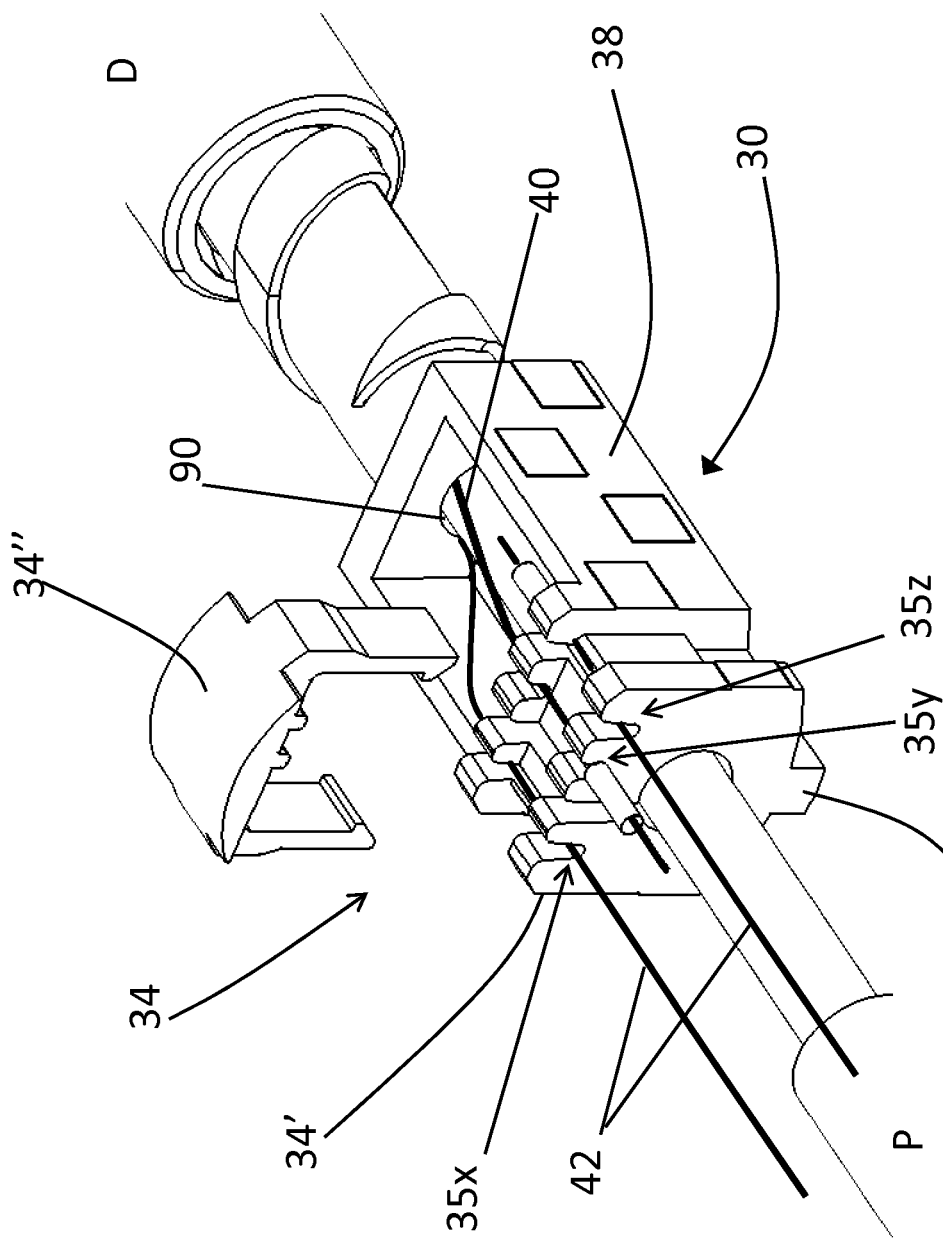
FIG. 3C is a top perspective view of a two-part slide, in accordance with an embodiment of the present invention.

In one embodiment of slide assembly 30, carriage 34 of the intermediate housing 38 may comprise multiple components that cooperatively engage or can be assembled to form the carriage 34. As an example of this, as shown in FIG. 3C and cross-sectional view 3D, the carriage 34 may have base portion 34' having grooves 35x, 35y and 35z through which wires 40 and 42 may be positioned, and a cover portion or a wire retainer 34" that engages with the base portion 34' after the wires have been placed to form openings or passages 35x', 35y' and 35z' through which control wires 40, 42 can slide. The cover portion 34" may be detachably secured to the base portion 34' for example using a snap fit arrangement. The cover portion 34" may comprise downwardly extending projections or legs 36, as shown in FIG. 3E, which are received within a groove 37 within the carriage base portion 34'. Legs 36 may have tabs, such as snap-fit tabs, that may interlock with a surface of groove 37 to secure cover portion 34" to base portion 34'.

Additionally, as shown in FIG. 3E, the base portion may comprise a groove 35w through which the control wires 40 and 42 may be routed after exiting the sheath 90 to assist in placement of the wires through each of the grooves 35x, 35y and 35z. The cover portion 34" may additionally comprise one or more teeth or ribs 35a that interact with the grooves 35x, 35y and 35z to partially form the passages or openings 35x', 35y' and 35z' to retain the wires therein. In one example, the cover portion 34" comprises two ribs or teeth 35a. In other embodiments the grooves may be positioned within the cover portion 34", or still in other embodiments grooves may be positioned within both the base portion 34' and the cover portion 34" as shown in FIG. 3E. In other words, either the base portion 34' and/or the cover portion 34" may receive wires 40, 42 and abut to form openings 35x', 35y' and 35z' within which wires can travel longitudinally. In one example, as shown, control wire 42 may be routed through openings or passages 35x' and 35z' that are located towards the exterior or opposing lateral edges of the slide assembly 30 to prevent excessive stress or strain on the control wire 42 and may help prevent the slide assembly 30 from rotating within the inner housing 20a (Whereas wire 40 is routed through opening or passage 35y'). More specifically, the control wire 42 is routed proximally through the slide assembly 30 through passage 35x', wrapped around the pulley and routed distally through the slide assembly 30 through passage 35z to be coupled to the distal face of the carriage 34. In other embodiments, wires 42 and 40 may be routed through any of the openings or passages within the slide.

Figure 3F:
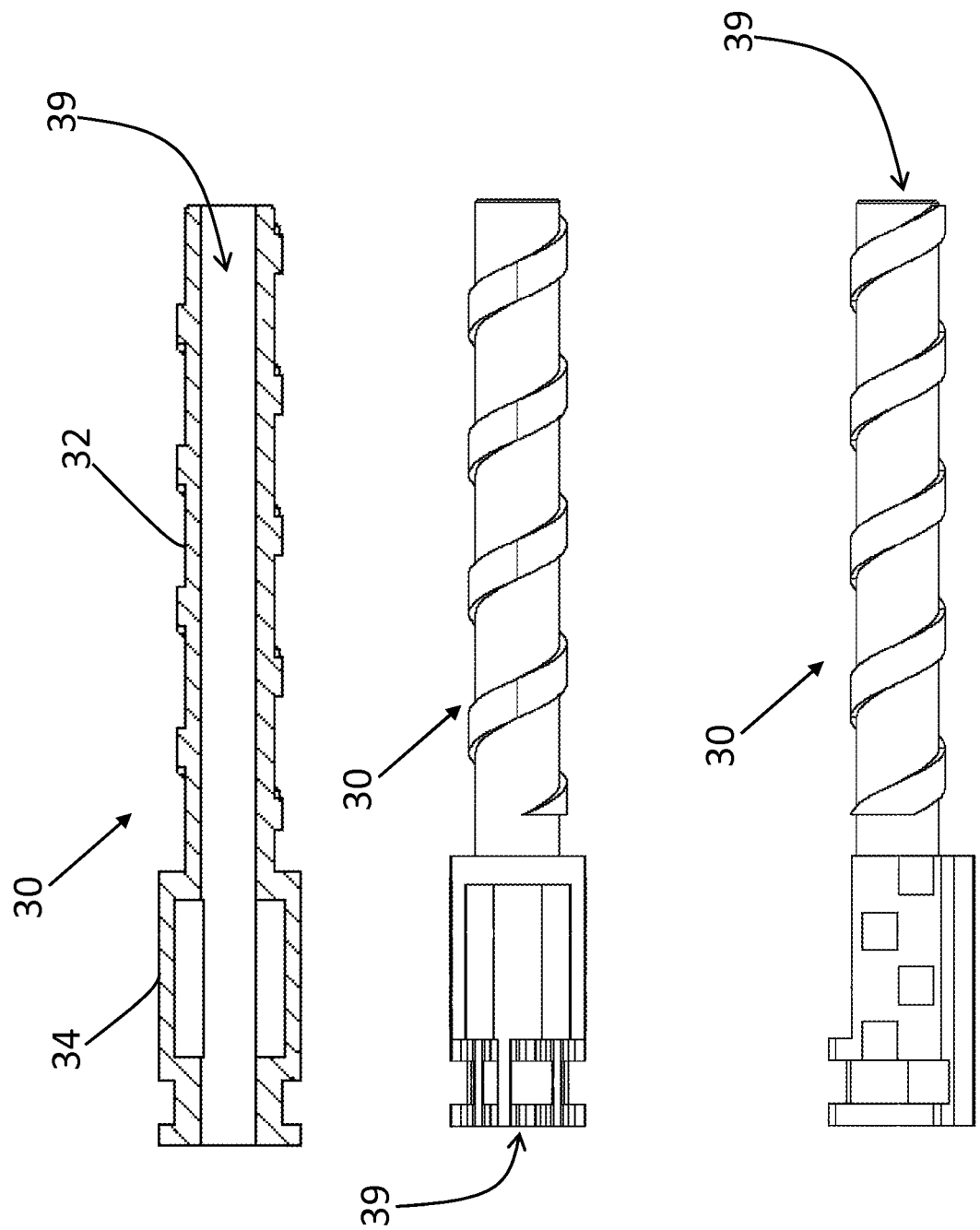
FIG. 3F illustrates a top cross-sectional view, a top view and a side view of a slide assembly, in accordance with an embodiment of the present invention.

In some embodiments for example in the embodiments illustrated in FIGS. 3A-3F, the slide assembly 30 comprises a channel 39 [shown in FIG. 3F] that extends through the bolt 32 as well as through the carriage 34 to allow a portion of the sheath 90 to be routed there-through. In a specific example, the sheath 90 extends through substantially the entire length of the handle 100 including the knob 10 as well as the housing 20.

Example 2: Integrally Formed Slide Assembly

Figures 3G, 3H:
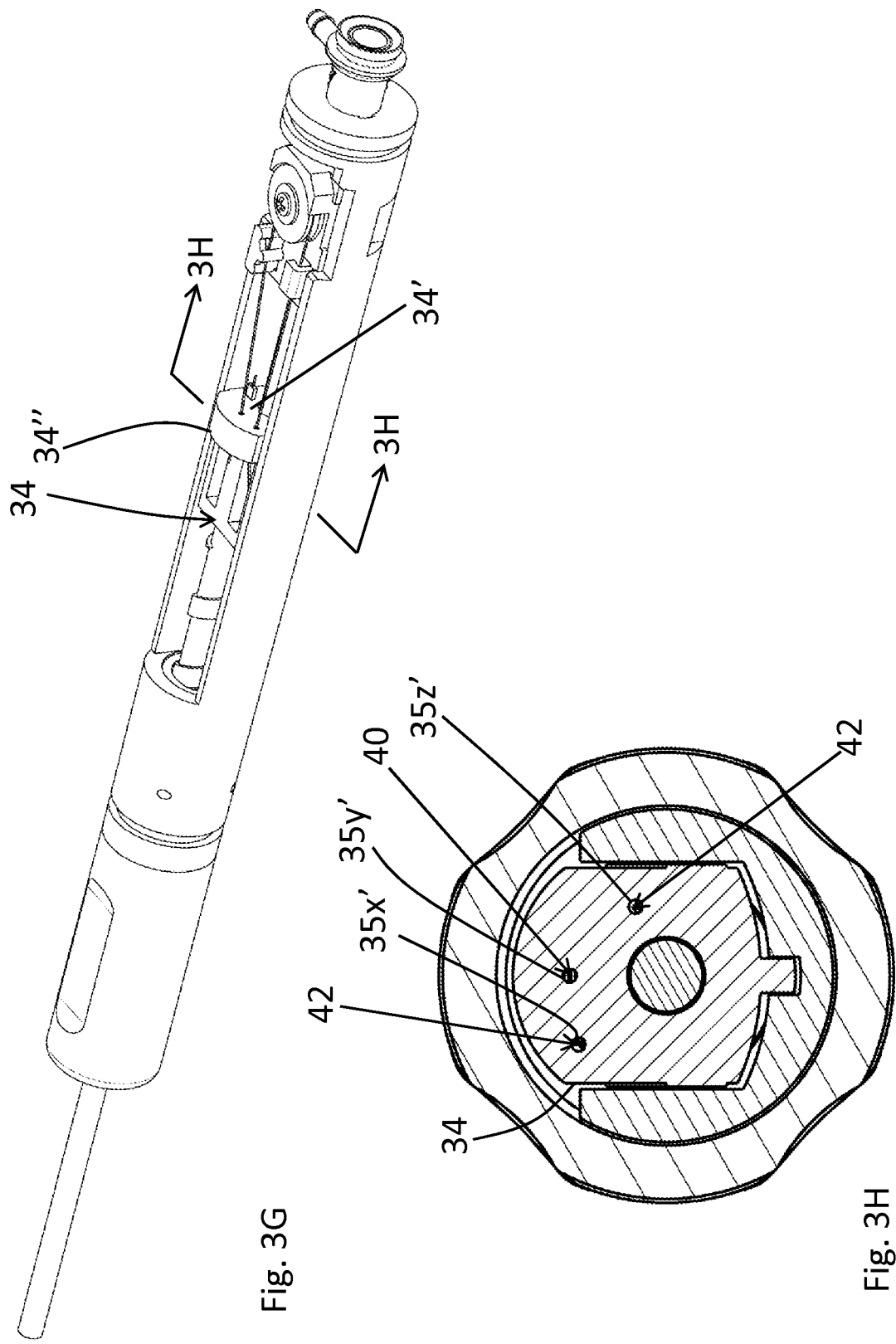
FIG. 3G is a perspective view of an internal handle assembly with a slide assembly in accordance with an alternative embodiment of the present invention.
FIG. 3H is a transverse cross-sectional view of a slide assembly taken along line 3H-3H of FIG. 3G, in accordance with an alternative embodiment of the present invention.

Alternatively, as shown in FIG. 3G, the base portion 34' and cover portion 34" may be formed integrally with one another. In other words, the carriage 34 may be of unitary construction and is formed of a single component. Similar to the embodiment described previously, the carriage 34 may comprise three channels or openings 35x' 35y', and 35z' through which wires 40 and 42 can be threaded respectively as shown in the cross-sectional view of FIG. 3H. In one example, control wire 42 is routed through openings 35x' and 35y' and control wire 40 is routed through opening 35z', in a manner similar to the one described herein above.

Alternative Embodiments of Slide Assembly

As discussed above, slide assembly 30 of handle 100 (as shown in FIG. 4A) comprises a bolt 32 having an externally threaded arrangement which is received within the knob 10 having a corresponding internally threaded arrangement. As shown in FIGS. 4B and 4C, this allows the knob 10 to translate the carriage 34 of the slide assembly 30 as it is rotated. In one example, the external thread of the bolt 32 may be in the form of a helical thread 33a that co-operatively engages with an internal helical thread 13 the inner knob 10a. In some examples, the helical thread 33a may be a continuous external thread as shown in FIG. 3F and FIGS. 4B-4C. This may provide more surface contact between the thread 33a of bolt 32 and internal thread 13 of inner knob 10a. This may enhance the friction between the bolt 32 and the inner handle and may allow for enhanced control. After the knob 10 has been rotated the enhanced friction may aid in maintaining the position of the knob 10 with respect to the housing to retain the sheath 90 at its desired deflection. Alternatively, the bolt 32 may have a discontinuous thread along its length. In some embodiments, the slide assembly 30, including bolt 32 is formed from a polymer. More particularly, in one example the slide assembly 30 comprises Dupont™ Delrin® 100P. Alternatively, the slide assembly 30 may comprise a thermoplastic. In still other embodiments, the slide assembly may comprise a metal. In some embodiments bolt 32 of the slide assembly 30 may have a rough exterior surface to maintain frictional engagement with the inner knob 10a. In some embodiments, bolt 32 with external threads 33a is coated with a lubricant such as a fluorocarbon gel 807. In one embodiment, the exterior thread of the bolt 32 may have tapered edges that form an overhang or the thread may have bevelled which may facilitate manufacturing of the slide assembly 30 for example through molding.

Overview of the Direction Reversing Element

Figure 5A:
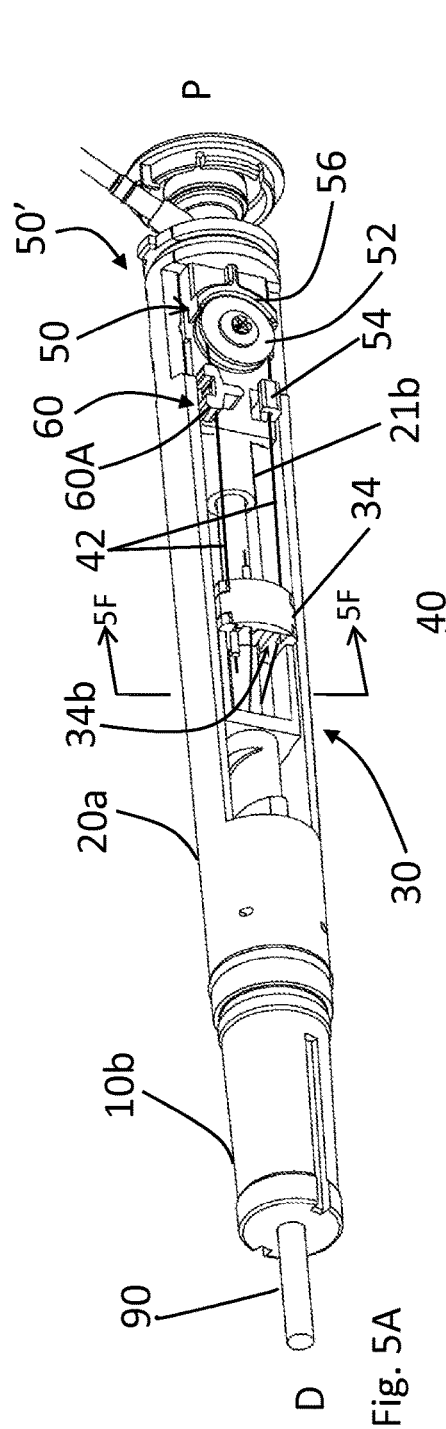
FIG. 5A shows a top perspective view of a pulley assembly inside a handle in accordance with an embodiment of the present invention.

As mentioned above, wire 42 is passed through a direction reversing element prior to being coupled to the slide assembly 30. In a specific example, as shown in FIG. 5A, the wire 42 as it exits the sheath 90 is passed in a proximal direction through the carriage 34 and then around a direction reversing element 50' so that it can be passed distally through the carriage 34 to be coupled to the distal face 34b of the carriage 34. In one specific embodiment, the direction reversing element comprises a pin. In another specific embodiment, as shown, the direction reversing element comprises a pulley assembly 50 comprising a pulley 52, also shown in the cross-sectional view of FIG. 5G. The pulley assembly 50 maybe coupled to the inner housing 20a using a snap fit. More specifically, with reference to FIG. 5A, the wire 42 as it exits proximally from carriage 34, it is routed over the pulley assembly 50 around the pulley 52 and passed distally through carriage 34 to be coupled to its distal face 34b. This is also illustrated in FIGS. 5B and 5C.

Example 1: Pulley Assembly

Figure 5B:
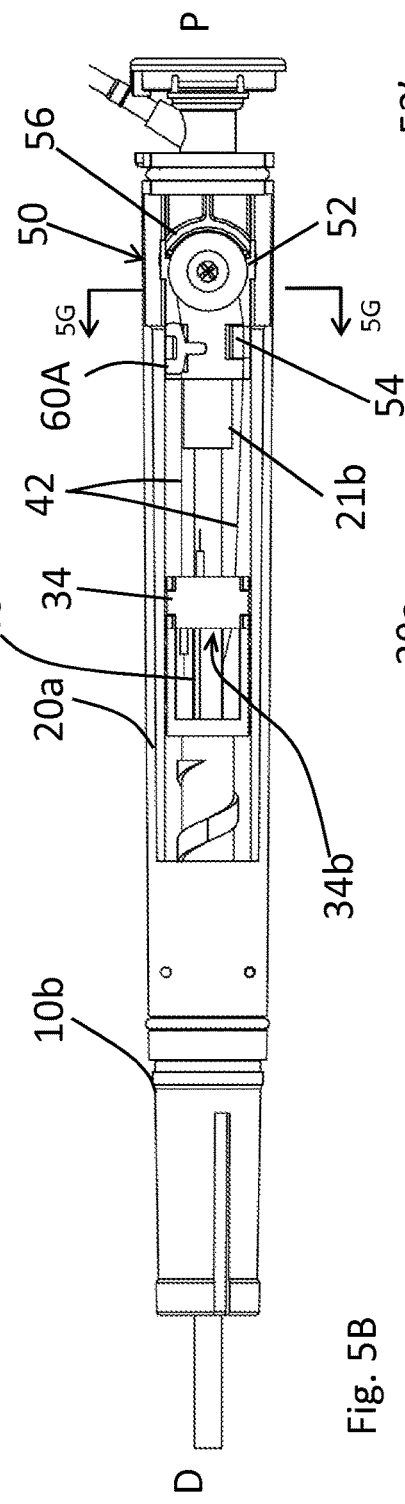
FIG. 5B illustrates a top view of a pulley assembly within a handle in accordance with an embodiment of the present invention.
Figure 5C:
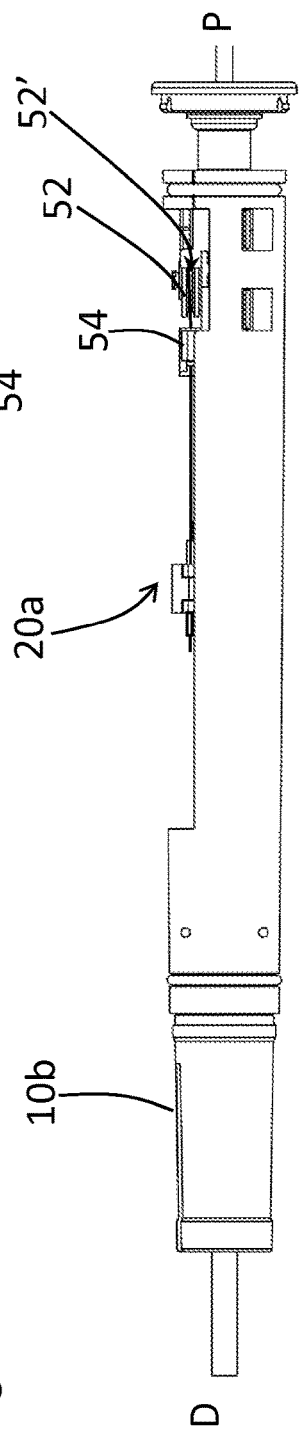
FIG. 5C illustrates a side view a pulley assembly within a handle in accordance with an embodiment of the present invention.
Figure 5D:
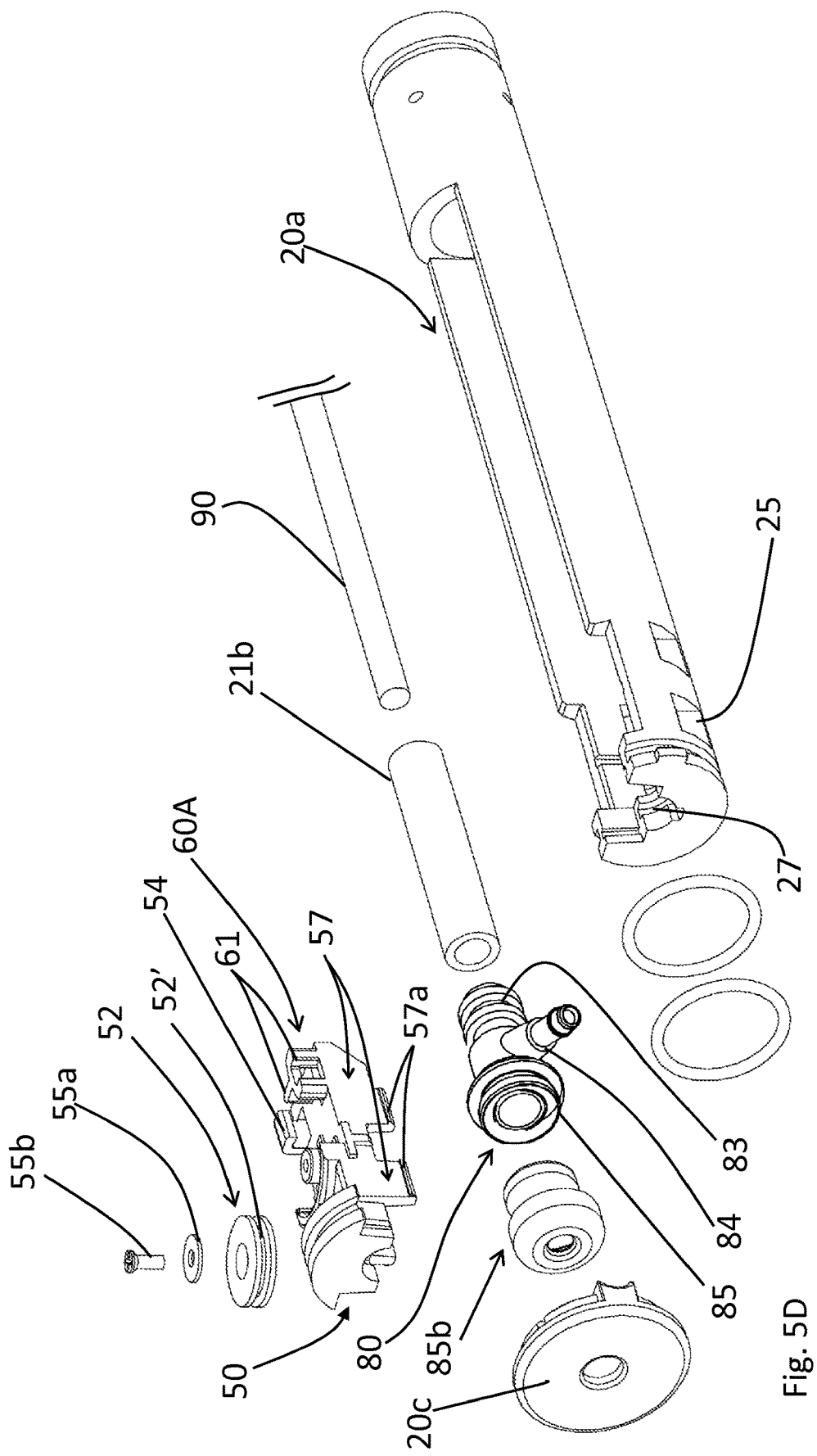
FIG. 5D is an exploded view of a handle showing a pulley assembly, in accordance with an embodiment of the present invention.

In one specific embodiment, as shown in FIGS. 5A-5B and 5D, the pulley assembly 50 comprises height guide 54 that helps maintain or secure the control wire 42 around the pulley 52. The height guide 54 may prevent the control wire from slipping or slide off the pulley 52 by maintaining its position along the plane of the pulley 52. In one example, the pulley 52 may comprise a groove or slot along its circumference to allow the control wire 42 to remain in place. The groove or slot 52' functions to guide and maintain the control wire 42 around the pulley 52. Additionally a pulley guide 56 may be provided that is substantially adjacent to and circumferentially surrounds at least a portion of the pulley 52. The control wire 42 is guided around the pulley so that it is positioned between the pulley 52 and the pulley guide 56. The pulley guide 56 functions to guide and trap the control wire 42 around the pulley 52 in order to maintain its position. Thus, the height guide 54 and the pulley guide 56 help to retain the control wire 42 about the pulley. As illustrated in FIG. 5E, the pulley guide 56 may additionally comprise teeth or projections 56a that additionally restrict the movement of the control wire 42 to further reduce the chances of misalignment of the control wire 42 and prevent the control wire 42 from falling off the pulley 52. The teeth or projections 56a extend from the pulley guide 56 inwardly towards the pulley 52 to control movement of the control wire 42, as shown in FIG. 5E. By providing one or more projections 56a between the pulley guide 56 and the pulley 52, the amount of friction between the control wire 42 and the pulley guide 56 is increased. In some examples, this may allow the pulley 52 to function as a pin. In some embodiments, each of the pulley 52, height guide 54 and the pulley guide 56 may be separate components or may be formed integrally with the pulley assembly 50, as shown. In one specific example as shown in FIGS. 5A-5E, and in the cross-sectional view shown in FIG. 5F, the pulley 52 is mounted on a pin 53 of the pulley assembly 50. A washer 55a and bolt 55b may be used to affix the pulley 52 to the pulley assembly 50. The pulley assembly 50 may co-operatively engage with the inner housing 20a. In one example, the washer 55a may comprise stainless steel and bolt 55b may be a self-threading screw that comprises steel.

In one embodiment, the pulley assembly 50 is detachably coupled to the inner housing 20a of the handle 100. In one example, the pulley assembly 50 is coupled to the inner housing 20a using a friction fit. More specifically, the pulley assembly 50 is coupled to the housing 20 using a snap fit arrangement. In one example, the pulley assembly 50 may comprise four legs 57 (two on each side of the pulley assembly 50), with each of the four legs 57 having laterally extending projections 57a that engage with corresponding openings 25 within the inner housing 20a, as shown in FIG. 5D. In one example, the pulley assembly 50 may be coupled to the inner housing 20a, after the sheath 90 is inserted along the inner housing 20a. The sheath 90 may be coupled to a hub 80 which may also be partially positioned within the inner housing 20a. In one example the hub 80 comprises a snap fit 85 for engaging with a hub cap 85b. In one example, the hub 80 comprises ribs 83 and one or more keys that co-operatively engage or lock with corresponding grooves 27 within inner housing 20a. This provides a rotational locking mechanism that prevents rotational displacement of the sheath 90 with respect to the handle 100. Once the sheath 90 with hub 80 have been positioned within the inner housing 20a, the projections of the pulley assembly 50 may then co-operatively engage with openings 25 within the inner housing 20a. This may allow the hub 80 to be locked longitudinally so that the longitudinal movement of the sheath 90 with respect to the inner housing 20a is limited. Thus in some embodiments, the control handle 100 provides both a rotational locking mechanism as well as a longitudinal locking mechanism for the sheath 90. In some embodiments, the hub 80 includes a port 84 that extends from the hub 80 and is encased within the outer housing 20b. In some embodiments, the pulley assembly 50 including the pulley 52 may comprise a biocompatible material such as a polymer. In one example, the polymer is Dupont™ Delrin®. In a specific example, the pulley assembly 50 comprises Dupont™ Delrin® 100P.

Example 2: Pin

In an alternate example, the direction reversing element may comprise a pin or other structure for routing or redirecting an elongate element such as a pull wire. In such an example, the wire 42, as it exits proximally from carriage 34, may be routed over and/or around the pin and passed distally through carriage 34 to be coupled to its distal face 34b of the carriage 34. In a specific example, the pin extends perpendicularly to the plane in which control wire 42 travels. In some embodiments, the pin is positioned proximally relative to the slide assembly 30. For example, the pin may be coupled to a proximal portion of the handle assembly 100. Alternatively, the pin may be positioned on the slide assembly 30 or be coupled to the slide assembly 30. In embodiments where a pin is used, the control wire 42 that is routed proximally from the carriage 34 may be looped around the pin so it can be routed distally to be coupled to the distal face 34b of the carriage 34.

Slack Limiting/Containing Element

In an embodiment of the present invention, one or more slack limiting or containing elements 60 may be provided within the handle 100 that may be coupled to one or both of the control wires 40, 42. In a specific example, a slack limiting element 60 is provided that allows frictional engagement of control wire 42 to limit or contain slack to a portion of the control wire 42. In one example, the slack limiting or containing element 60 is coupled to the pulley assembly 50, as shown in FIG. 5A.

Serpentine Friction Device

In one specific embodiment, the slack limiting or containing element 60 may comprise a serpentine friction device 60A as shown by FIGS. 4D-4F and FIGS. 5A-5E. The serpentine friction device 60A comprises pins 61 (as shown in FIG. 5D) that extend perpendicularly to the path of the control wire 42 as shown in FIG. 5E-5F and FIG. 6A. As further shown in FIGS. 6A-6B, the control wire 42 is directed or weaved through spaces, gaps or openings 61s defined by the pins 61 and held in place by the pins 61. The serpentine friction device 60A may comprise pins 61 that are off-centred from each other (for example laterally offset) and may partially overlap each other with respect to the longitudinal axis of the control wire 42. In a specific example the serpentine friction device 60A comprises three pins 61. The two outer pins 61(a) and 61(c) may be positioned such that they are off-axis from a central pin 61(b), as illustrated in FIG. 6B. As further illustrated in FIGS. 6A-6B, in a specific example, the serpentine friction device comprises pins that are attached to each other along a top portion 66. In other embodiments, the serpentine friction device 60A may comprise ribs or raised surfaces with which the wire frictionally engages. Control wire 42 may be weaved through the ribs such that it frictionally engages the ribs.

In another example, as shown in FIGS. 7A, 7B and 7C, the serpentine friction device 60A may comprise two portions a base portion 62 and a top portion 66 with the pins 61 extending between the base portion 62 and the top portion 66. The control wire 42 may be threaded through openings 61s between each of the pins 61 and the top portion 66 may be used to secure control wire 42 in place. Alternatively, each of the pins 61 are formed integrally with the base portion 62 and top portion 66, respectively and control wire 42 may be threaded through openings 65 prior to being coupled to the slide assembly 30. Still furthermore, the pins 61 may only be attached to a base portion 62.

Biased Friction Device

Figure 8B:
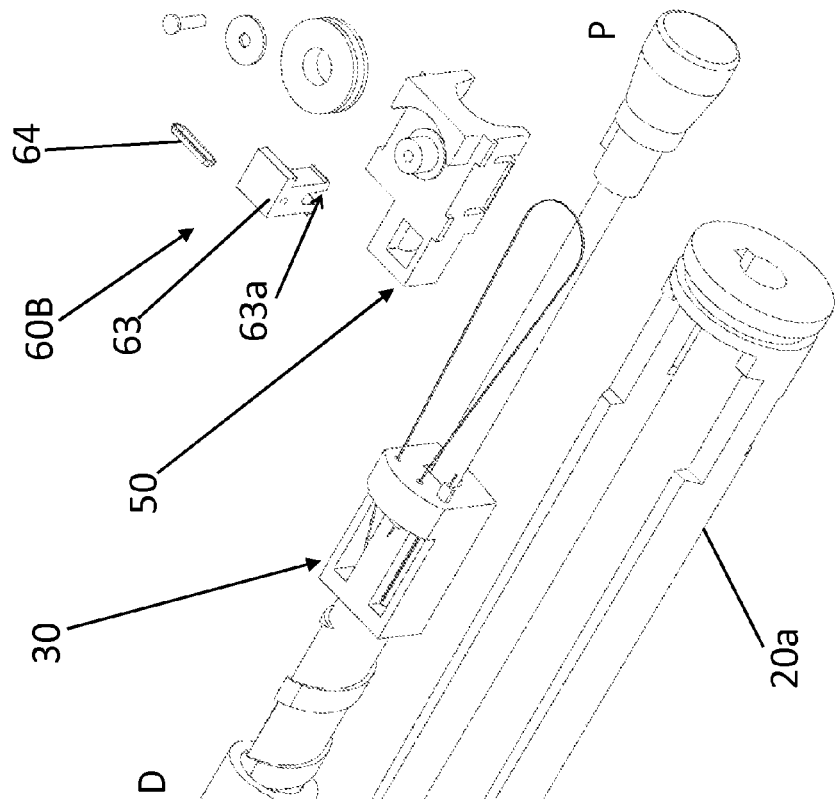
FIG. 8B is an exploded view of a handle assembly with an alternate embodiment of a slack limiting or containing element in accordance with an embodiment of the present invention.
Figure 8A:
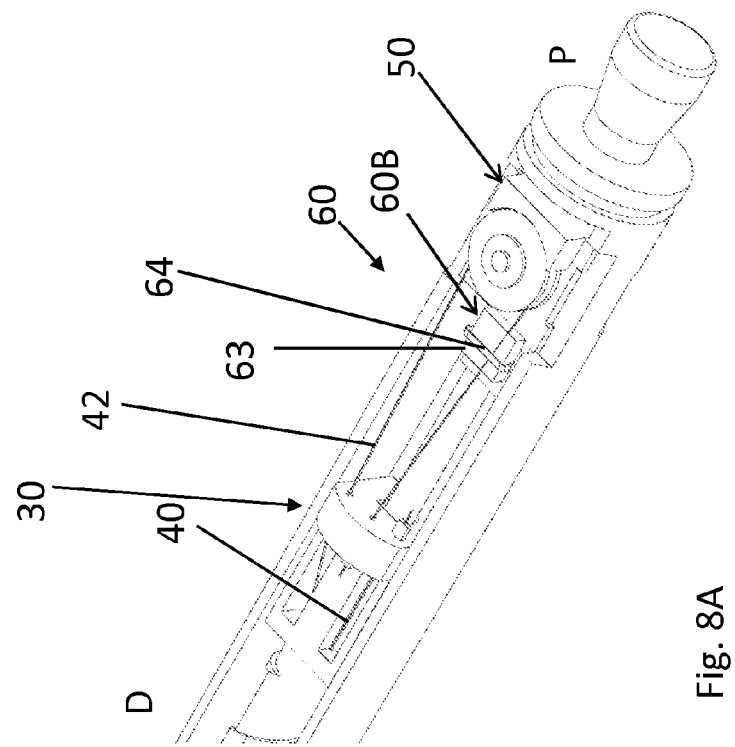
FIG. 8A is a perspective view of an alternate embodiment of a slack limiting or containing element, in accordance with an alternate embodiment of the present invention.

In an alternate embodiment of the present invention, the slack limiting or containing element 60 comprises a friction device that is biased 60B as shown in FIGS. 8A and 8B. The biased friction device 60B may be coupled to the pulley assembly 50 that is operable to co-operatively engage with the inner housing 20a. In one example, the biased friction device 60B may be coupled to the pulley assembly 50 via a snap fit arrangement. The friction device 60B comprises a friction block 63 and clip 64 coupled to the friction block 63. The friction block 63 may define an opening 63a to receive the clip 64. The clip 64 may be biased towards the friction block 63. As mentioned previously, one or both of the control wires 40, 42 may be coupled to a biased friction device 60B. In one example, control wire 42 passes through the biased friction device 60B such that it is held between the clip 64 and the friction block 63. In one example, clip 64 comprises a spring biased mechanism. In some embodiments, the friction block 63 may comprise a polymer. In other embodiments the friction block 63 may comprise an elastomer and the clip 64 may comprise metal. In one example, the friction block 63 comprises rubber and the clip comprises a wire band and friction may be created between the wire band and the rubber. In some embodiments the bias mechanism of the clip 64, for e.g. spring may be adjustable or tunable.

Resilient Friction Device

In still another embodiment the friction device may comprise a resilient friction device 60C for frictionally engaging the control wire 42. In one example the resilient friction device 60C may comprise an elastomer block 67a as shown in FIGS. 9A and 9B. In one embodiment the elastomer block 67a may comprise a rubber block. The elastomer block 67a may define a slit 67b extending longitudinally along its length thereof. A control wire, for example, control wire 42 may be guided within the opening of slit 67b. The slit 67b may define two downwardly extending legs 68 of the elastomer block 67a. The control wire 42 may be frictionally engaged by the downwardly extending legs 68 and held between the legs 68.

Slide Restricting or Limiting Element

Example 1: Track within the Handle Housing

In some embodiments, the inner housing 20a is configured to guide the slide assembly 30 along a linear path within the inner housing 20a. In one example as shown earlier in FIGS. 3E and 4B, the inner housing 20a comprises a groove or track 21a that runs substantially along the length of the inner housing 20a. The slide assembly 30 may comprise a raised projection 31a (see, for example, FIG. 3E) along the base of the slide assembly 30 that co-operatively engages within the track 21a to aid in maintaining linear translation of the slide assembly 30 along the track 21a.

Figure 10A:
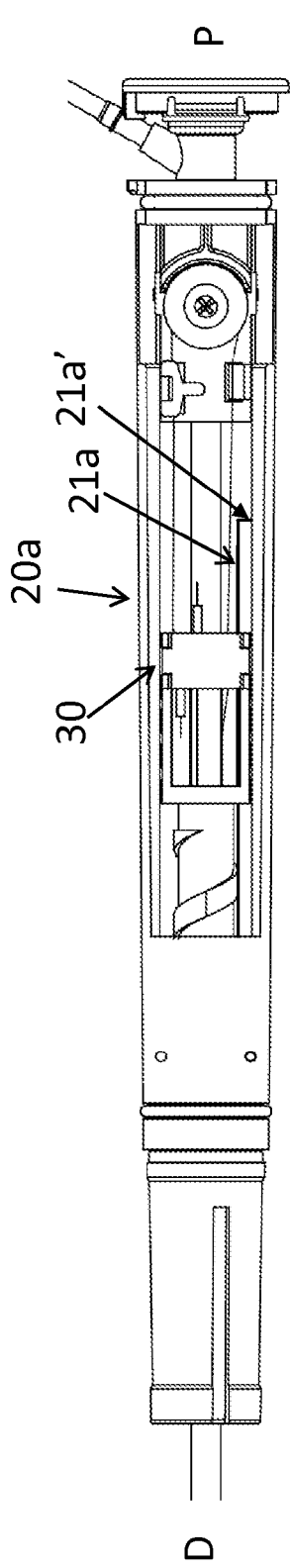
FIGS. 10A-10C illustrate various embodiments of a slide limiting feature or slide stop in accordance with various embodiments of the present invention.
Figure 10B:
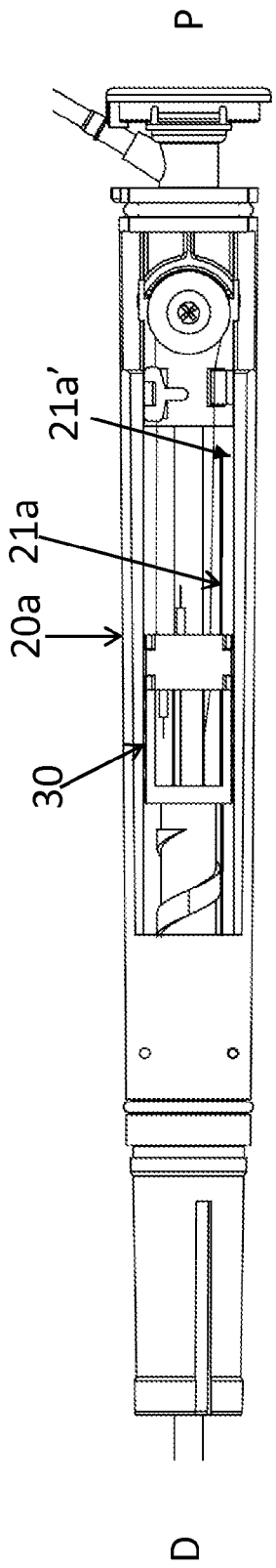

The track 21a may additionally function as a slide stop to restrict the movement of the slide assembly 30 to allow for a desired deflection of the sheath 90. In other words the length of the track 21a restricts the distance the slide assembly 30 may travel in a given direction (either in the proximal and/or distal direction) which may be used to restrict the amount of deflection of the sheath 90. The groove or track 21a defines an end wall 21a' on each of its two opposed ends as shown in FIGS. 4B and 10A. Once the raised projection 31a of the slide assembly 30 reaches the end of the track it abuts against the wall 21a' at the end of the groove or track 21a stopping the slide assembly 30 (As shown in FIG. 10a, the groove or track 21a functions as a slide stop in the absence of a tubular slide stop 21b discussed further herein below). FIGS. 10a and 10b illustrate grooves 21a of different lengths and as such the distance travelled by the slide assembly 30 is different for each of the embodiments shown in FIGS. 10a and 10b.

Figure 10C:
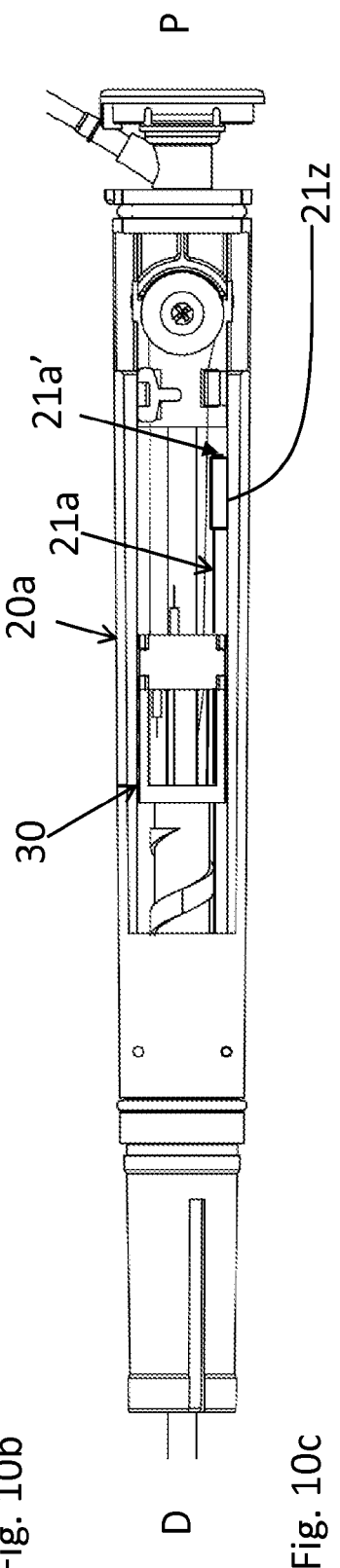

In a further alternative, an adjustable length stopper may be provided that is coupled to the track 21a (it may engage with the track 21a using a snap fit arrangement or may be coupled thereto using any other means such as friction fit or glue). The adjustable length stopper may comprise an arm extends out and can engage with the slide assembly 30 thus preventing translation of the slide assembly 30. In another example as shown in FIG. 10c, the adjustable length stop may comprise a pin 21z that may be inserted at the end of the groove or track 21a [for example inside the groove of FIG. 10b] next to wall 21a' to shorten the length of the track. In other words the pin 21z is provided for interacting with the track 21a to change the length of the track 21a. In some embodiments the pin 21z may be inserted within the track 21a proximal to the slide assembly 30. In other embodiments, the pin 21z may be inserted within the track 21a distal to the slide assembly 30. Still further, the adjustable length stopper may in the form of a block or an arm that may be affixed within the track and effectively functions to shorten the length of the track 21a.

Example 2: Tubular Slide Stop

Figure 10D:
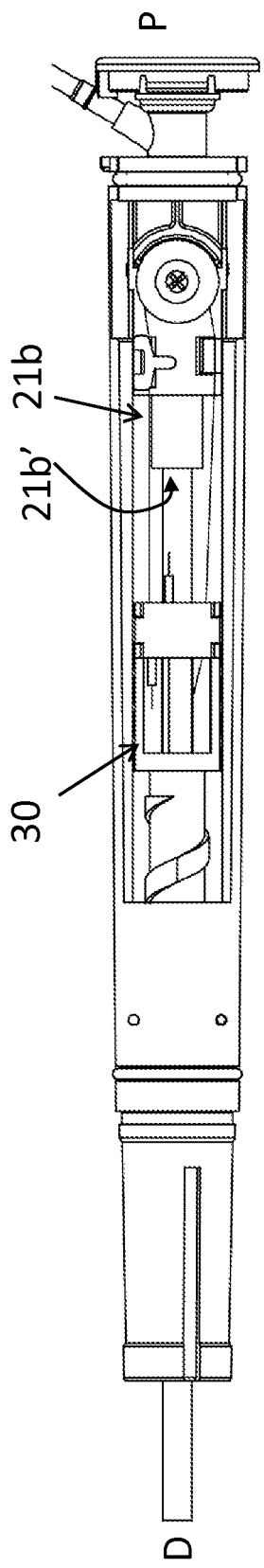
FIGS. 10D-10F illustrate alternate embodiments of a slide limiting feature or slide stop in accordance with various embodiments of the present invention.

In some embodiments, the slide restricting element comprises a tubular slide stop 21b as shown in FIGS. 2A-2C, 4B-4C, 5A, 5D and 10D. As an example, the tubular slide stop 21b is mounted over the sheath 90 on a proximal side of the slide assembly 30. In some embodiments, the tubular slide stop 21b may comprise a piece of hard or rigid tubing that abuts against a hub of the sheath and may comprise notches to allow engagement therewith and with the inner housing 20a. In one example, a glue joint may be provided between the tubular slide stop 21b and the hub on which it is mounted. In some embodiments, the surface contact between the tubular slide stop 21b and hub 80 may be enhanced for adhering the tubular slide stop 21b to the hub. In some embodiments, the tubular slide stop 21b may have additional notches for interacting with pulley assembly 50 and inner housing 20a. In some embodiments, as shown in FIG. 4B and FIG. 10d, the tubular slide stop 21b may abut against and/or interact with the pulley assembly 50. In other embodiments, the tubular slide stop 21b may be mounted over the sheath and may not be affixed. The tubular slide stop 21b may comprise a relatively flexible or soft/resilient material such as low-density polyethylene (LDPE). In some embodiments the tubular slide stop 21b may comprise a relatively harder or more rigid material. In a specific example, the tubular slide stop 21b comprises a high-density polyethylene (HDPE). Alternatively, the tubular slide stop may comprise stainless steel. In one example, the tubular slide stop 21b comprises a cylinder. Alternatively, the tubular slide stop 21b is formed from a segment of a cylinder. In some embodiments, the inner diameter of the tubular slide stop 21b may be larger than the outer diameter of the sheath 90 over which it is mounted. The tubular slide stop defines a distal wall 21b' that interacts with slide assembly 30 to stop it.

Figure 10E:
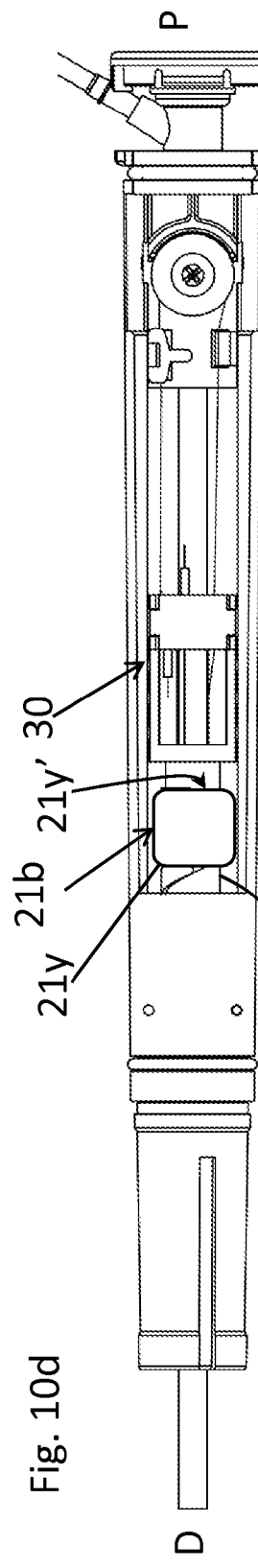

In still other embodiments as shown in FIG. 10e, the tubular slide stop 21b may be in the form of a collar 21y (defining a proximal wall 21y') that fits over the bolt 32 of the slide assembly 30 on a distal side of the slide assembly 30. Alternatively, the range of motion the slide assembly 30 may be altered by shortening or increasing the length of the bolt 32 of the slide assembly 30. In a further alternative, the tubular slide stop 21b may be formed as a part of the pulley assembly 50 and may extend there-from into the inner housing 20a.

Example 3: A Bar Extending Across the Inner Housing

Figure 10F:
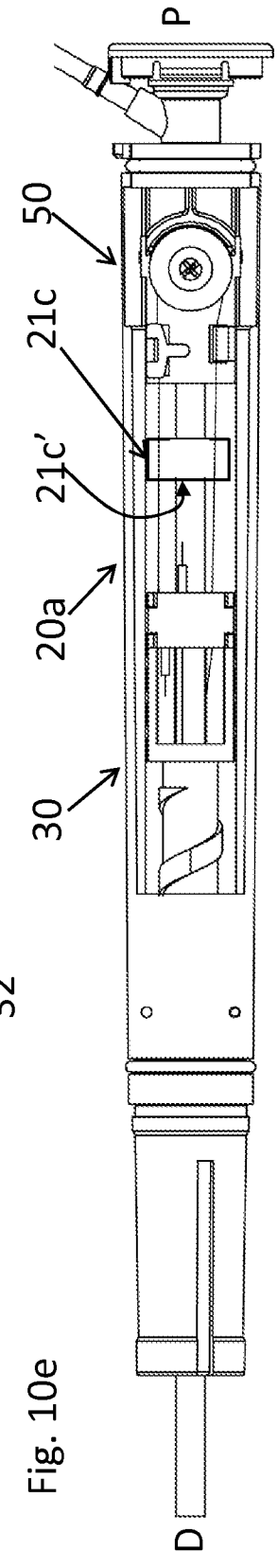

In alternative embodiments as shown in FIG. 10f, the slide stop or slide limiting or restricting feature may comprise a bar 21c extending laterally across the inner housing 20a. In other words, the bar 21c extends across the width of the inner housing 20a. The bar 21c may be positioned between the slide assembly 30 and the pulley assembly 50 with the bar defining a defining a distal wall 21c'.

Example 4: The Slide Stop Comprises a Rivet

Figure 10G:
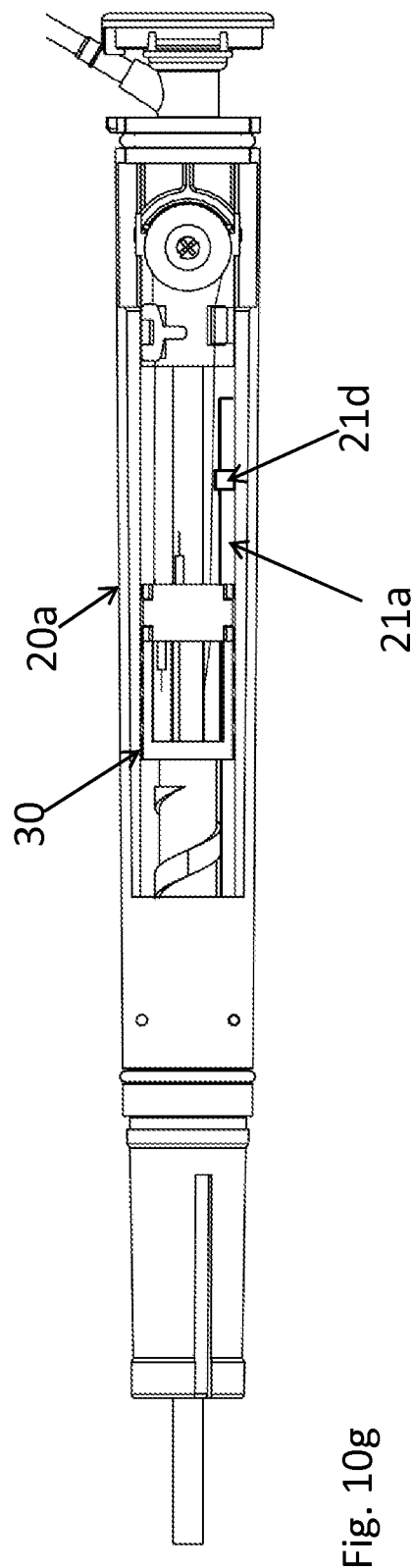
FIGS. 10G-10H illustrate additional alternative embodiments of a slide limiting feature or slide stop in accordance with various embodiments of the present invention.

In some embodiments, as shown in FIG. 10g, the slide stop may comprise a rivet 21d. Alternatively, the slide stop may be in the form of a pin or a screw. The rivet 21d is positioned through an opening within and the groove or track 21*a* within the inner housing 20*a* and extends into the lumen of the inner housing 20*a* in the form a projection that extends vertically up. The rivet 21*d* may be secured to the inner housing through a friction fit. The rivet 21*d* is positioned in the path of the slide assembly 30 and functions to restrict its movement. Alternatively, rivet 21*d* may be coupled to a secondary component such as a block that is positioned within the inner housing 20*a* and functions to block the slide assembly 30.

Alternatively, an actuator may be provided on the handle that allows adjustment of the slide limiting feature by the user prior to or during use so that the maximum radius of curvature of the sheath 90 in either one or both directions may be adjusted. In some embodiments the actuator may be in the form of a knob or a button.

Example 5: Slide Stop is an Extension of the Pulley Assembly

Figure 10H:
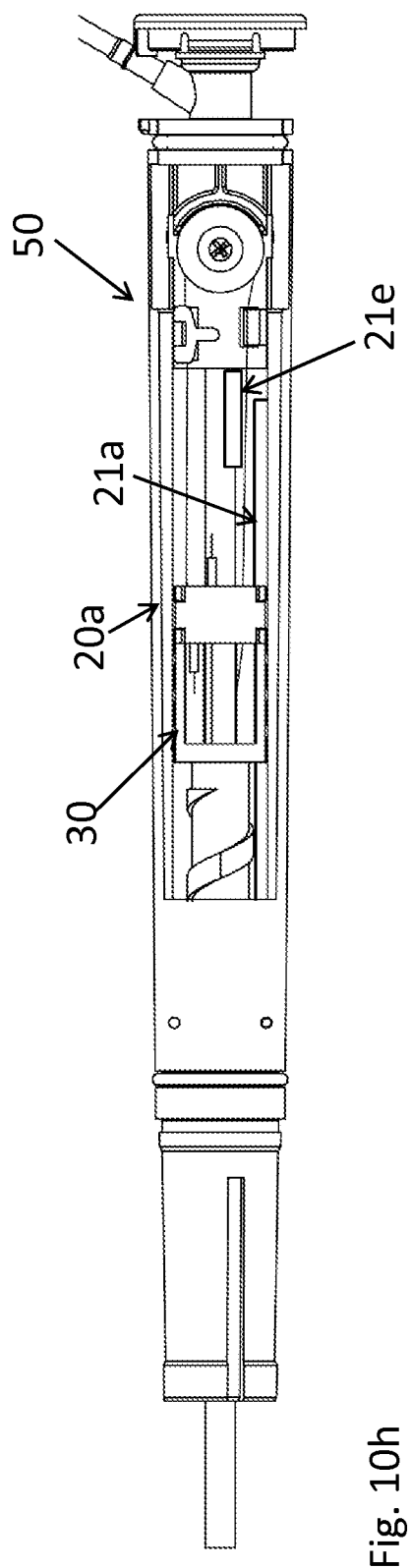

In a still further alternative, the slide restricting component or slide stop may comprise an extension 21*e* of the pulley assembly 50, as shown in FIG. 10*h* that extends distally into the lumen of the inner housing 20*a*.

Control Wires

In some embodiments, control wires 40, 42 comprise a metal. More specifically, in one example the wires 40, 42 comprise stainless steel. In some embodiments, the wires 40, 42 comprise a drawn 300-series stainless steel wire. In some embodiments, at least one of the control wires 40, 42 comprise a round wire. In other embodiments, at least one of the control wires 40, 42 comprise a flat wire which may be a rectangular wire. In one specific embodiment, the wires 40, 42 comprise stainless steel 304V. In one example, wires 40, 42 have a cross-section of about 0.004"×0.015". In another example, wires 40, 42 have a cross-section of about 0.004"× 0.012".

Crimps

Figure 11B:
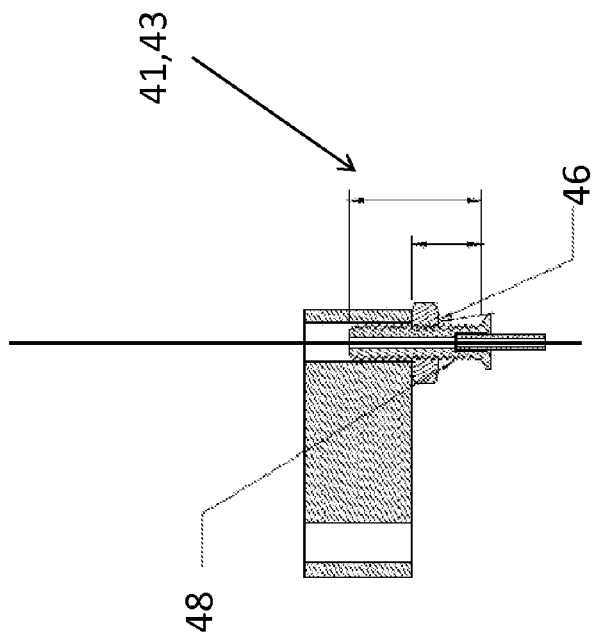
FIGS. 11A-11B illustrate an alternative embodiment of a crimp, in side and cross-sectional views, in accordance with an embodiment of the present invention.
Figure 11A:
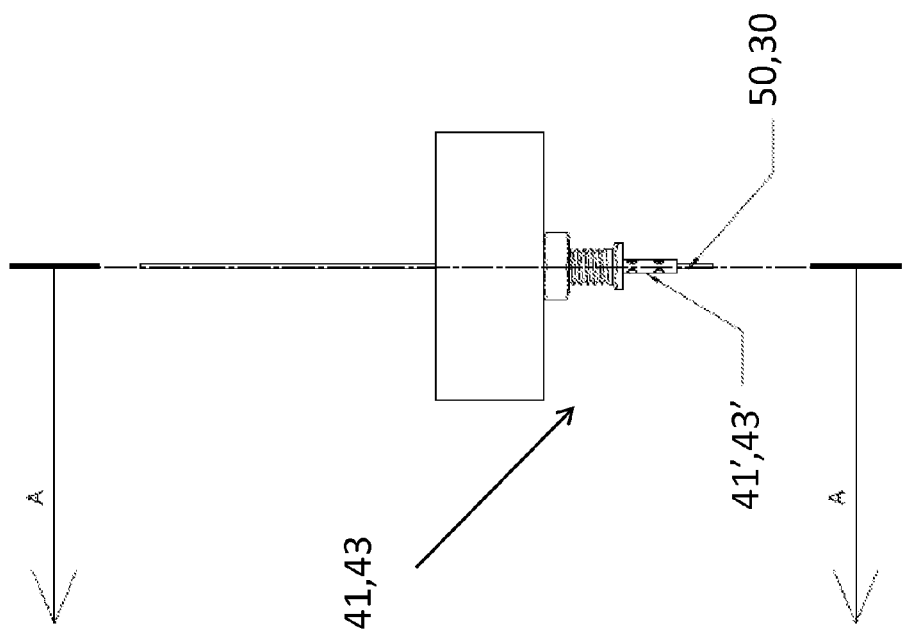

As shown in FIGS. 11A and 11B, in some embodiments the crimps 41, 43 may comprise an adjustable crimp. In one example, the adjustable crimp may comprise a nut and bolt assembly. In one embodiment, the adjustable crimp may comprise a bolt or screw 48 with external threads that co-operatively engage with internal threads within the nut 46. A cylindrical crimper part 41', 43' is held partially within the screw 48. The initial length of the wires 40 and 42 may be adjusted by adjusting the position of the screw 48 relative to the nut 46. In some embodiments one or more of the openings 35*x*' 35*y*' and 35*z*' within the carriage 34 may have a diameter sufficient to accommodate the bolt or screw 48. In other embodiments, crimps 41, 43 may not be adjustable crimps.

Sheath and Hub

In some embodiments, sheath 90 may extend through the handle 100 from the proximal to the distal end of handle 100 as shown in FIGS. 2A-2C. This is additionally illustrated in the cross-sectional view of FIG. 4B-4C. In one embodiment, the sheath 90 is coupled to a hub 80 at its proximal end as additionally shown in FIGS. 2C and 5D. The hub has a side-port 84 defining an opening there-through. In one example, the side-port 84 may be angled. In one embodiment, the side-port 84 may be at an angle of about 60° with respect to the longitudinal axis of the hub 80. In other embodiments, any other suitable angle may be used. As shown in FIG. 2C, the side-port is connected to a stopcock 92 for example a 3-way stopcock via tubing 94 which in one example may comprise polyurethane tubing. The angled side-port 84 may enhance usability of the handle 100 by ensuring that the side-port 84 and the stopcock 92 coupled thereto remain out of the way of the user, during use of the handle 100. In some examples, the side-port 84 may be used as a point of reference in order to orient the sheath 90 distal tip. In one example, the opening defined by the side port may allow physicians to inject fluid for e.g. saline or contrast through the sheath during the procedure. In one example, delivery of contrast from the side-port may allow for imaging during use, where the steerable handle assembly 100 is used to access a region of tissue within the patient's body.

In some embodiments the hub 80 may be encased within the outer housing 20*b* as shown in FIGS. 1, 2A-2C, 5D and cross-sectional views 4B-4C. An end cap 20*c* may be used to secure hub 80 within the inner housing 20*a*. In one embodiment, the end cap 20*c* may comprise a polymer. In a specific example, the end cap 20*c* comprises polypropylene. The sheath hub 80 may be operable to receive a dilator for insertion into the sheath.

Locking Mechanism

In one embodiment, a locking mechanism may be provided to lock the position of the handle knob 10 with respect to the housing 20, in order to maintain a specified angle of deflection of the sheath tip. In one embodiment a slider lock may be provided. In other embodiments friction fit or frictional engagement between the threads 13 of the inner knob 10*a* and the threads of the bolt 32 of the slide assembly 30 (as shown in FIGS. 4B and 4C) may provide sufficient frictional force in order to maintain the position of the knob 10 to aid in maintaining the desired deflection of the sheath 90. In one example, the slide assembly 30 including the bolt 32 and carriage 34 may have a surface finish that provides sufficient friction to maintain the desired deflection and hence the position of the sheath distal end. In one example, the slide assembly 30 and/or the lumen of the internally threaded knob 10 may have a rough surface finish to enhance the friction between the two. In one example, both the inner knob 10*a* and the slide assembly 30 comprise Dupont™ Delrin® 100P as noted hereinabove.

Additionally, in some embodiments as shown in FIG. 2C, a chamfer or groove 16 may be provided within the inner knob 10*a*, at the interface between the inner knob 10*a* and the inner housing 20*a* to allow a resistance or frictional element such as an o-ring 16' to be placed therein. This may enhance friction between the inner knob 10*a* and the inner housing 20*a* to maintain the position of the inner knob 10*a* with respect to the inner housing 20*a* after it has been rotated. In other words, the o-ring 16' allows for retention of the curve of the sheath 90 after it has been steered or deflected. In one embodiment, the o-ring may comprise a polymer. In other embodiments the o-ring may comprise a Nitrile. In a specific embodiment, the o-ring may comprise BUNA-N. In another example, the o-ring comprises a fluoroelastomer such as Viton®. In some such embodiments, a lubricant or dampening grease may be applied to the o-ring to dampen noise or in other words to prevent squeaking as the inner knob 10*a* is rotated with respect to the inner housing 20*a*. In a particular example the lubricant comprises a synthetic hydrocarbon grease such as Nyogel 767A. Alternatively, a washer, for example a Teflon washer may be inserted over the inner knob 10*a* at the interface between the outer knob 10*b* and the inner housing 20*a* to reduce friction. In some additional embodiments, one or more o-rings 28' may be provided as shown in FIG. 2C that are received within one or more grooves 28 within the inner housing that provide an interface or a seal between the inner housing 20*a* and the outer housing 20*b*. In some embodiments, one of the grooves 28 may be formed partially within the inner housing 20a and partially within a component within the inner housing 20a, such as within a segment of the pulley assembly 50.

Overview of the Operation of the Handle Assembly

In use, the sheath 90 may be inserted within the vasculature of a patient's body and advanced to a target location. The handle 100 may then be manipulated to allow the user to deflect a distal portion of the sheath 90 in the desired direction. In one broad embodiment, a rotational mechanism is provided that allows rotational movement of the knob 10 in one direction to allow longitudinal movement of the slide assembly 30 in one direction within the inner housing 20a (away from a neutral or starting position) to place one of the control wires 40, 42 in tension. This allows the sheath distal end to be deflected in a first direction. Whereas, rotation of the knob 10 in a second direction releases the tension in that control wire and allows the sheath 90 to return to its neutral position. Further rotation of the knob in the second direction allows the slide assembly 30 to translate linearly or longitudinally in the other (opposing) direction within the inner housing 20a allowing the other of the two control wires 40, 42 to be placed in tension. This allows the sheath distal end to be deflected in a second direction.

Figure 4D:
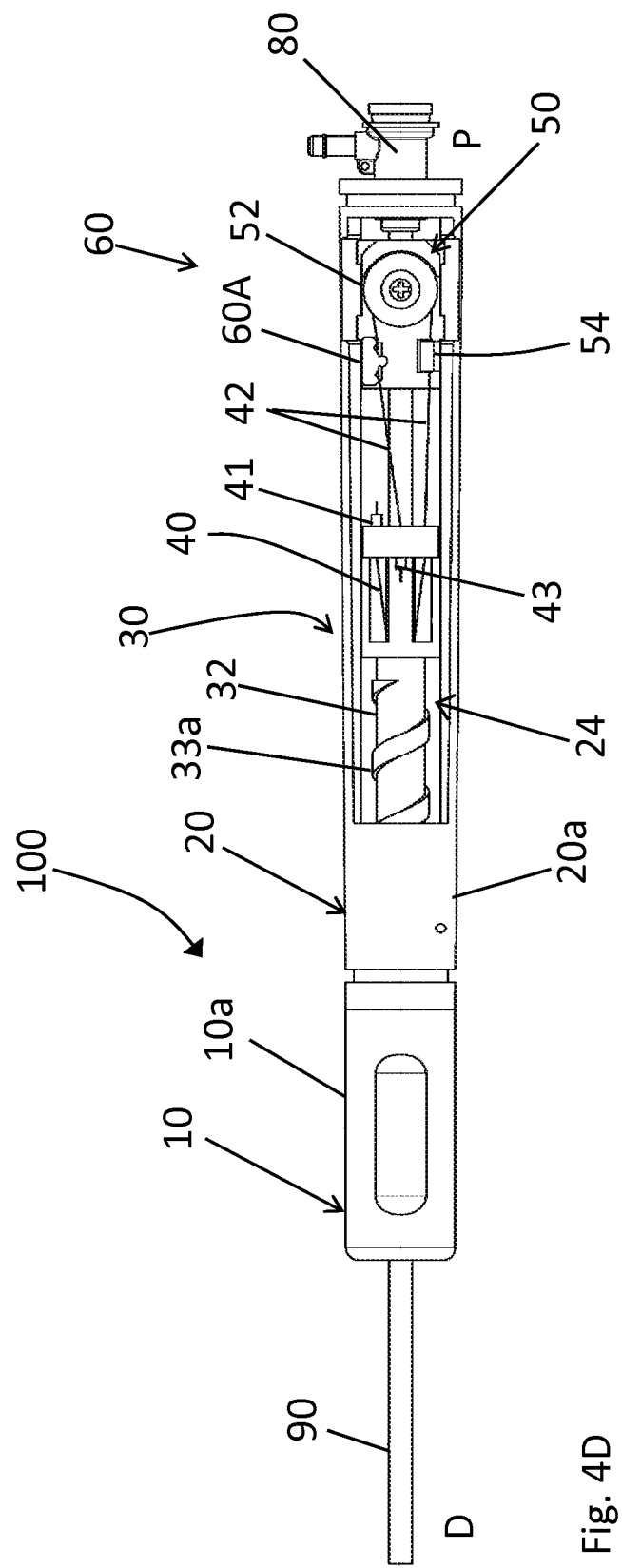
FIGS. 4D, 4E and 4F illustrate operation of a handle assembly in accordance with an embodiment of the present invention.
Figure 4E:
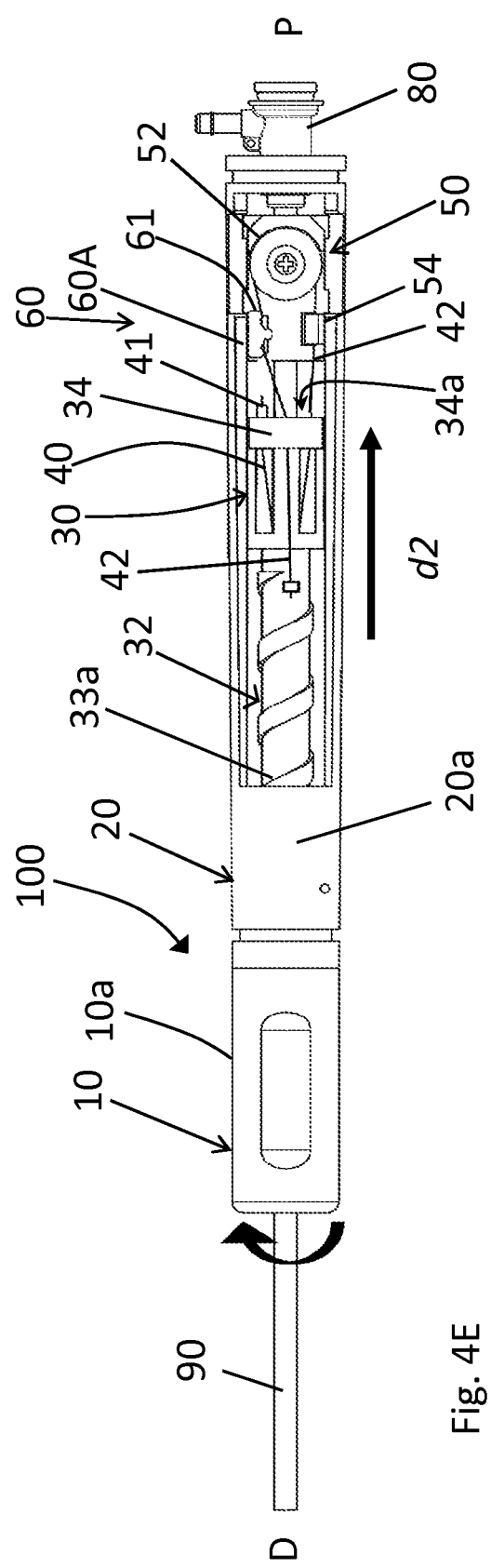

More specifically, with reference to FIG. 4D, handle assembly 100 is shown with the slide assembly 30 positioned in the neutral position. As the handle knob 10 is rotated in a first direction (for example clockwise) as shown in FIG. 4E, the internal threads 13 of the internal knob 10a [illustrated previously in FIGS. 4B and 4C] engage with external threads 33a of bolt 32 of the slide assembly 30. As shown in FIG. 4E, rotation of the knob 10 translates the slide assembly 30 including carriage 34 linearly in a proximal direction (P) within the internal housing 20a. In other words the slide assembly 30 moves longitudinally towards the proximal end (shown by direction d2) of the handle 100. As the carriage 34 moves proximally within the internal housing the proximal face 34a of the carriage 34 abuts against the crimp 41. As the knob 10 is rotated further in the clock-wise direction, movement of the carriage 34 causes the crimp 41 to translate proximally, pulling control wire 40 and placing it in tension. As the control wire 40 is placed in tension it causes a deflection in a distal end portion of the sheath 90 to which it is coupled, thus steering the sheath 90 in a first direction in a desired plane. In other words, as control wire 40 is pulled taut and placed in tension, as shown in FIG. 4E, it allows the curvature of the sheath tip to change. A deflection of the distal end of the sheath 90 in a first direction may be observed. Furthermore, as wire 40 is placed in tension, control wire 42 remains in a neutral or relaxed state. Additionally, as the carriage 34 moves towards the proximal end of the handle 100 upon rotation of the knob 10, slack may be created in control wire 42.

Figure 4F:
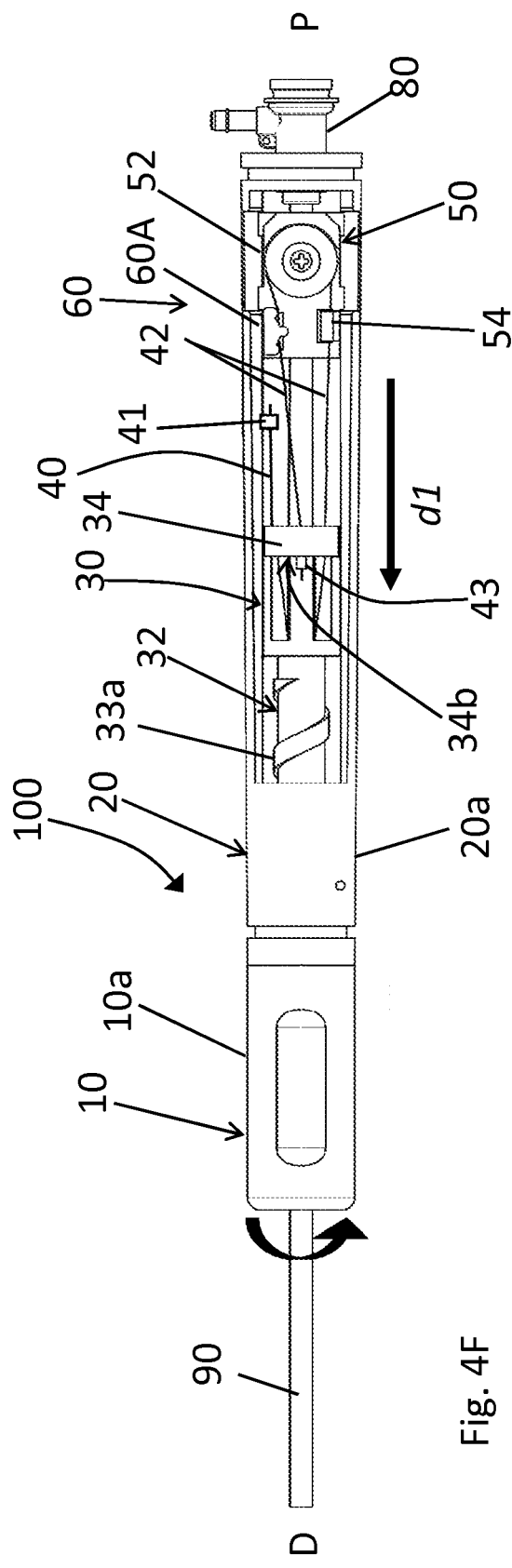

Similarly, as the knob 10 is rotated in a second direction (for example in a counter-clockwise direction) as shown in FIG. 4F, the internal threads 13 of the internal knob 10a [previously illustrated in FIGS. 4B and 4C] engage with external threads 33a of the bolt 32 of the slide assembly 30. As shown in FIG. 4F, rotation of the knob 10 causes the slide assembly 30 and thus carriage 34 to translate linearly within the internal housing 20a in a distal direction (D). As the carriage 34 moves distally, the strain or tension in the wire 40 is released and a gradual reduction in the distal end deflection of the sheath 90 is observed. The sheath 90 may reach its neutral position where no stresses are observed in either wire 40 or 42.

As the carriage 34 moves further distally within the internal housing 20a, the distal face 34b of the carriage 34 abuts against crimp 43. As knob 10 is rotated further counter-clockwise, the translational movement of carriage 34 results in translation of the crimp 43, pulling the control wire 42 and placing it in tension as shown in FIG. 4F. As the control wire 42 is placed in tension it causes a deflection in the distal end portion of the sheath or catheter 90 to which it is coupled, thus steering the sheath 90 in a second direction. In one embodiment, the sheath 90 may be manipulated in a second direction that is within the same plane as the first direction. In other embodiments sheath 90 may be deflected in a separate plane.

Operation of Slack Limiting or Containing Element

As mentioned above, in some embodiments, a means may be provided for preventing or limiting any slack created in control wire 42 from travelling to the segment of control wire 42 that is in contact with the pulley 52. As outlined above in FIG. 4E, as knob 10 is rotated in a clockwise direction, carriage 34 travels proximally placing tension on control wire 40 while releasing tension from control wire 42. In some embodiments, a slack limiting or containing element 60 may be provided to limit or contain any slack in control wire 42 as tension is removed from the wire 42 (or in other words during reverse manipulation of the control wire 42). In some embodiments, the slack limiting or containing element 60 engages a proximal portion of the control wire 42. Similarly, as knob 10 is rotated in a counterclockwise direction as shown previously in FIG. 4F, the carriage 34 travels distally placing tension on control wire 42 and releasing control wire 40 from tension. In one embodiment, a slack limiting or containing element 60 may be provided to limit or contain slack in control wire 40. In some embodiments, the slack limiting or containing element 60 may also limit or contain any slack in wires 40, 42 due to compression of the shaft of the steerable sheath 90 during use. In some embodiments of the present invention the slack limiting or containing element may frictionally engage either one of the control wires 40, 42. In some embodiments, each of the pull or control wires 40, 42 may be guided through a slack limiting or containing element 60 to reduce slack in a segment of the wires 40, 42 or to direct slack away towards a specified direction.

In some embodiments as described above, the slack limiting or containing element 60 is coupled to the pulley assembly 50 and affects control wire 42 that passes through it. The slack limiting or containing element 60 functions to prevent any slack generated in wire 42 from traveling to or affecting the segment of wire 42 that is positioned around the pulley 52. Thus, the segment of control wire 42 positioned around the pulley remains substantially taut preventing control wire 42 from slipping from around the pulley 52. In one example, the slack limiting or containing element comprises a serpentine friction device 60A as illustrated in FIGS. 4D-4F. The serpentine friction device is further illustrated in FIGS. 5A-5E, 6A-6B and 7A-7C as described previously.

Operation of the Serpentine Friction Device

In one embodiment, as shown in FIG. 4F a slack limiting or containing element 60 is used that may encourage any slack created in wire 42 to travel distally (shown by direction d1) through its opening or passage within the slide assembly 30. In other words any slack in the control wire 42 or in other words, the slackened control wire 42, moves distally with respect to the carriage 34 through its respective opening. This may help prevent slack from affecting the segment of control wire 42 around the pulley 52. Thus, the slack limiting or containing element 60 may prevent excess slack in the wire around the pulley 52 and may help reduce the risk of the control wire 42 from derailing from the pulley 52. In some embodiments, where the pulley 52 has a groove to guide control wire 42 around pulley 52, the slack limiting or containing element 60 may function to maintain the control wire 42 in position.

In one example, the handle or device 100 includes a serpentine friction device 60A as outlined herein above and as illustrated in FIGS. 5A-5E, 6A-6B and 7A-7C. The serpentine friction device 60A as further illustrated in FIG. 4E, allows for one-way travel of the wire. The wire can travel in one direction (e.g. d1, distal direction) with greater ease that in the second direction (proximal direction d2). When the knob 10 is rotated clockwise, wire 40 is placed in tension, and slack is created in control wire 42. The serpentine friction device 60A prevents control wire 42 from slipping or travelling proximally, thus the segment of control wire 42 around the pulley 52 remains taut. In other words tension is maintained in the segment of control wire 42 around the pulley 52 which minimizes the risk of control wire 42 from derailing from the pulley 52. In other words friction provided by the serpentine friction device 60A restricts movement of the control wire 42 in the proximal direction and ensures any slack in control wire 42 is guided distally. The friction between control wire 42 and pins 61 is sufficient such that in the absence of an active pull force on the control wire 42, the control wire 42 cannot overcome the force of friction. Thus, control wire 42 cannot travel in the proximal direction as shown in FIG. 4E and any slack created in wire 42 travels in the distal direction d1 through its respective opening. However, when tension is applied on the control wire 42 as shown in FIG. 4F upon counter-clockwise rotation of the knob 10 (after the slide assembly 30 has reached its neutral position), sufficient force is applied such that it overcomes the force of friction present between wire 42 and pins 61 thus allowing movement of the wire around the pulley 52 to allow control wire 42 to be placed in tension. Control wire 42 is actively pulled in the distal direction d1.

Operation of the Biased Friction Device

In one embodiment the slack limiting or containing element comprises a biased friction device 60B comprising a friction block 63 and clip 64 as described herein above with respect to FIGS. 8A and 8B. During operation, when the knob 10 is rotated clockwise tension is placed on control wire 40 through proximal movement of slide assembly 30 from its neutral position and slack is generated in control wire 42. In the absence of tension applied to control wire 42 the force exerted by the friction block 63 and clip 64 is sufficient to prevent proximal movement of the control wire 42 such that slack created in control wire 42 cannot be transmitted to the segment of control wire 42 around the pulley 52. In other words the segment of wire 42 around the pulley 52 remains in tension. However, upon counter-clockwise rotation of the knob the slide assembly 30 moves distally back to its neutral position and upon further counter-clockwise rotation of the knob, the slide assembly 30 moves distally from its neutral position and force is applied to wire 42. When sufficient force is applied to wire 42 distally, such that the applied force is greater than the frictional force exerted by friction device 60B onto control wire 42, the control wire 42 can translate longitudinally under tension. In one example, the control wire 42 can translate longitudinally in a distal direction under counter clockwise rotation of the knob 10. In summation, the longitudinal movement of the control wire 42 in a proximal direction may be prevented under clockwise rotation of the dial as control wire 42 is released from tension and control wire 40 is placed in tension. Thus, slack generated in control wire 42 can be guided away from the pulley using the biased friction device 60B, minimizing the risk of control wire 42 falling off from the pulley 52.

Operation of Resilient Friction Device

Similar to the operation of the biased friction device 60B described above, as shown in FIGS. 9A and 9B, the resilient friction device 60C comprising elastomer block 67a frictionally engages the control wire 42 within the slit 67b between legs 68 of the elastomer block 67a. The friction device 60C permits distal movement of control wire 42 under tension as the slide assembly moves distally, but provides a sufficient frictional force such that the wire control wire 42 is unable to move longitudinally in a proximal direction when it is in a relaxed state during proximal movement of the slide assembly 30. Thus, when control wire 42 is inactive (not under tension), the segment of control wire 42 around the pulley 52 still remains taut as slack is not transmitted to this segment. This is a result of the frictional forces imparted on control wire 42 by the resilient friction device 60C.

General Overview of Operation of the Handle Assembly

In one embodiment, as shown in FIGS. 4A-4C, the control handle 100 may allow the bi-directional deflection of the sheath 90. In one example, in the neutral position the carriage 34 may be positioned distal of the center of the inner housing 20a. In such an example, a sheath tip curvature in the range of about 0-180° may be achieved when the knob 10 is rotated in a clockwise direction and about 0-90° sheath tip curvature may be achieved when the knob 10 is rotated in a counter-clockwise direction. In one embodiment, a left-hand tip response may be observed with a clock-wise or right hand knob rotation. In other embodiments, a right-hand tip response may be observed with a clock-wise or right hand knob rotation. The degree of curvature that is achieved in each direction may be adjustable by changing the neutral or starting position of the slide assembly 30 in combination with a slide limiting element for limiting the range of translation of the slide assembly 30. In some embodiments, the sheath may be defected to about 270 degrees in at least one of the two deflection directions. In other embodiments a greater than 270 degree curvature may be achieved.

Mechanism for Adjustable Handle Stroke Using a Slide Limiting Element

Example 1: Slide Limiting Element is the Track

As outlined above, the track 21a within the inner housing 20a can additionally function as a slide stop to restrict the movement of the slide assembly 30 to allow for a desired deflection of the sheath 90. As shown in FIG. 10a, once the slide assembly 30 (for example a raised projection 31a of the slide assembly 30 shown in FIG. 3E) reaches the end of the track it abuts against a wall 21a' at the end of the groove or track 21a, thereby stopping or limiting linear motion of the slide assembly.

In some embodiments, the length of the track 21a may be adjustable to alter the degree of deflection that may be provided in the sheath 90 using the handle 100. Thus in some embodiments a shorter track 21a may be provided in the inner housing 20a as shown in FIG. 10a, providing a shorter translation distance for the slide assembly 30 resulting in a more limited range of motion for the sheath 90. In other words the sheath 90 is provided with a reduced maximum deflection angle or stroke length. The track 21a may be shortened through insertion of a pin 21z as shown in FIG. 10c. Once a portion of the slide assembly 30 abuts against the pin 21z, the pin 21z prevents further translation of the slide assembly. In other embodiments a longer track 21a may be provided in the inner housing 20a as shown in FIG. 10b, providing a longer translation distance for the slide assembly 30 resulting in a wider range of motion for the sheath 90. In other words the sheath 90 may be provided with a greater maximum deflection angle or stroke length. In general, the length of the track 21a may restrict the distance the slide assembly 30 can travel in a given direction (either in the proximal and/or distal direction) which may be used to restrict the amount of deflection of the sheath 90.

In one specific example, the slide stop may be positioned proximal to the slide assembly 30 and may restrict translation of the slide assembly 30. However, this restriction in the movement of the slide assembly 30 may be used to limit the deflection of the sheath 90 in either proximal and/or the distal direction. This may be achieved by altering the neutral position of the slide assembly 30. A neutral position [N] of the slide assembly is illustrated in FIG. 4B. In one specific example, the neutral or starting position of the slide assembly 30 is adjustable which may determine the allocation of the range of motion of the slide assembly 30 in each of the distal and proximal directions. In other words adjusting the neutral or initial position of the slide assembly 30 determines the distance the slide assembly 30 may travel in each of the distal and proximal directions determining the amount of deflection of the sheath 90 in each of its deflection directions. In some embodiments, the neutral position may be adjusted in combination with the use of a slide stop to provide a sheath 90 capable of 90° degrees of rotation in each of its deflection directions (or in other words, sheath 90 has a stroke length of 90° degrees in each direction). Alternatively, sheath 90 may be capable of undergoing a 180° degrees of deflection in each direction. In other embodiments the sheath 90 may have a deflection angle of 90° degrees in one direction and a deflection angle of 180° degrees in the other direction. Thus, the sheath 90 may have a matching radius of curvature/deflection or stroke length in both directions or a varying radius of curvature/deflection in each direction. In still another alternative, the sheath has a deflection angle of up to about 270 degrees in at least one of its deflection directions. In other embodiments the sheath may have a deflection angle that is more than 270 degrees. In embodiments of the present invention as described herein, the slide limiting element is a component that is separate from the slide assembly 30.

Example 2: Slide Limiting Element is a Tubular Slide Stop

In some embodiments as described previously, the slide limiting element comprises a tubular slide stop 21b as shown in FIGS. 2A-2C, 4B-4C, 5A and 10D. The use of a longer tubular slide stop 21b results in a more restricted movement of the slide assembly 30. In one example, the tubular slide stop 21b is positioned proximal to the slide assembly 30. In some embodiments the tubular stop 21b comprises a relatively hard material and is substantially rigid such that it does not yield substantially under application of force. In one such example, upon clockwise rotation of the knob 10, as slide assembly 30 translates proximally within the inner housing 20a the slide assembly 30 abuts against the wall 21b' of a rigid tubular slide stop 21b preventing further translation of the slide assembly 30. This provides tactile feedback which may be experienced as a hard stop by the user. This may help indicate to the user that the maximum deflection of the sheath 90 has been achieved. Alternatively, in some embodiments as described above the tubular slide stop 21b may comprise a softer or resilient material that yields gently when the slide assembly 30 abuts against the wall 21b' preventing further translation of the slide assembly 30. This provides tactile feedback which may be experienced as a soft or gentle stop by the user. This may indicate to the user that the sheath 90 is close to reaching its maximum deflection. In one example, the tubular slide stop 21b may have a diameter that is substantially greater than the outer diameter of the sheath 90 over which it is mounted. In one embodiment as shown in FIG. 10e, the tubular slide stop 21b is positioned distal to the slide assembly 30 and is in the form of a collar 21y defining proximal wall 21y'. In one example the collar 21y comprise a rigid material. For example under counter clockwise rotation of knob 10, slide assembly 30 travels distally and is stopped by the wall 21y' of the collar 21y.

In some embodiments, where the tubular slide stop 21b has an inner diameter that is greater than the outer diameter of the sheath 90. The tubular slide stop 21b may help retain a curve of a stiff medical device such as a rigid needle that may be advanced through the sheath 90. The tubular slide stop 21b may prevent the curve from being straightened by reducing constraint against the sheath 90.

Example 3: Slide Limiting Element Comprises a Bar

As described previously, in some embodiments the slide limiting element or slide stop comprises a bar 21c extends with the inner housing 20a along a transverse plane. In one example, the bar 21c is positioned between the slide assembly 30 and the pulley assembly 50. The bar 21c impedes or restricts the movement of the slide assembly 30 as it abuts against wall 21c' of the bar, thus restricting the total translation distance available to the slide assembly 30. This consequently restricts the amount of tension that can be placed on one or more of the wires 40, 42 and thus limiting the deflection of the sheath 90.

Example 4: Slide Limiting Element Comprises a Rivet

As described above, in some embodiments the slide limiting element may comprise a rivet extending into the lumen of the inner housing 20a at a point along the track 21a. The rivet 21d may be positioned through an opening in the track 21a and held in frictional engagement therein. The rivet blocks the path of the translating slide assembly 30 and effectively shortens the length of the track 21a. In one example of this, there may be multiple openings or holes provided within the track 21a and the position of the rivet 21d may be adjustable. In other words, the rivet 21d may be positioned in any one of the openings. This may allow enable the user to vary the length of the track 21a and the desired translation distance of the slide assembly 30 and consequently the desired distal end deflection of the sheath 90. In some embodiments, the rivet 21d works in conjunction with a secondary component to block the movement of the slide assembly 30. The rivet secures the secondary component within the lumen of the inner housing 20a. In some examples of this, the longitudinal length of the secondary component may be adjustable to vary the translation range of the slide assembly 30 and consequently the deflection of the sheath 90. Alternatively, an actuator may be provided for example for activating a mechanical means for changing the length of the secondary component to adjust the maximum allowable translation of the slide assembly 30.

Example 5: A Slide Stop Formed as an Extension of the Pulley Assembly

As discussed above, and as shown in FIG. 10*h*, in a still further alternative, the slide restricting component or slide stop may comprise an extension 21*e* of the pulley assembly 50 that extends distally into the lumen of the inner housing 20*a*. The extension 21*e* functions to impede movement of the slide assembly as described herein above to limit the defection of the sheath 90.

Mechanism for Providing Unidirectional Control of a Bi-Directional Steerable Catheter Having Two Deflection Directions Overview of the Bidirectional Steerable Catheter With reference now to FIG. 12A, in accordance with one embodiment of the present invention, a catheter control system or handle 200 is illustrated for use with a bidirectional steerable sheath or catheter 90. As shown in FIG. 12A, the steerable catheter handle 200 is similar structurally and in operation to the handle 100 discussed previously. Handle 200 comprises an actuator comprising a knob 10 (comprising inner and outer knobs 10*a*, 10*b* respectively) that is coupled to a housing 20 (comprising inner and outer housings 20*a*, 20*b*). The inner knob 10*a* has internal threads that co-operate with external threads 33 of the bolt 32 of the slide assembly 30, shown in FIG. 12B. Upon actuation in a first direction, for example upon rotation of the knob 10 in a first rotational direction, the handle 200 is operable to move slide assembly 30 in a first linear direction within the inner housing 20*a* to tension one of the two control wires 40, 42 that are coupled to the carriage 34 of the slide assembly 30 via crimps. Upon actuation in a second direction, for example rotation of the knob 10 in a second rotational direction the handle 200 is operable to move the slide assembly 30 in a second linear direction within the inner housing 20*a* to tension the other of the two control wires 40, 42.

In some embodiments, the sheath or catheter 90 may have a total length that is equal to between about 90.5 cm to about 91.5 cm, and more specifically that is equal to about 91 cm. In one such example, the usable length of the catheter or sheath 90 (which the length of the catheter that is distal to the handle 200) may be about 70.5 cm to about 71.5 cm. More specifically, the usable length is equal to about 71 cm. In another example the usable length of the catheter 90 may be equal to about 44.5 cm to about 45.5 cm, and more specifically the usable length is equal to about 45 cm. In one such example, the total length of the sheath may be equal to between about 64.5 cm to about 65.5 cm, and more specifically the total length may be equal to about 65 cm. In alternative embodiments, catheter 90 may have a length that varies from between about 70 cm to about 92 cm, with a usable length that varies from between about 44 to about 72 cm. In still other embodiments, the catheter 90 may have a length that is less than about 70 cm with a usable length that is less than about 44 cm. In still other embodiments, the catheter may have a length that is greater than about 92 cm with a usable length that is greater than about 72 cm. In further embodiments catheter 90 may a have other lengths and usable lengths as may be known to a person skilled in the art.

A Unidirectional Control System Using a Slide Limiting Element Positioned Proximal to the Slide Assembly Some embodiments of the present invention comprise a unidirectional control system for providing unidirectional control of a bi-directional steerable catheter having at least two deflection directions, the control system comprising an actuator coupled to at least two control wires, wherein the actuator actively actuates the first control wire to tension the first control wire to deflect the bi-directional steerable catheter from a neutral position in a first deflection direction, and wherein the actuator actively actuates the second control wire to tension the second control wire to un-deflect the steerable catheter towards its neutral position to allow the bi-directional steerable catheter to return to its original position.

Figure 12C:
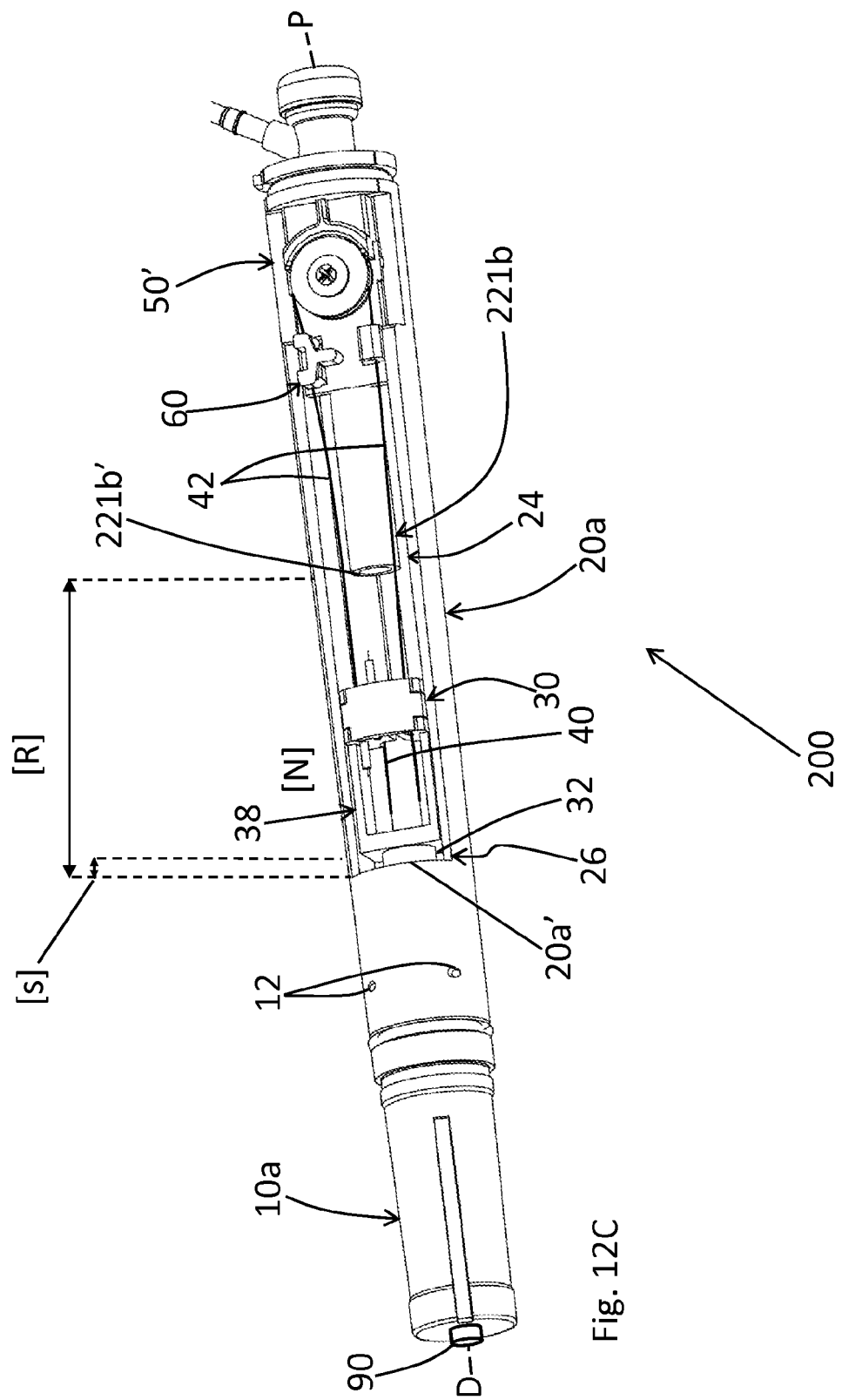

In the embodiment shown in FIGS. 12A and 12B, the handle 200 additionally comprises a deflection limiting mechanism for limiting deflection of the steerable catheter 90 in one of its two deflection directions. In some embodiments the deflection limiting mechanism comprises a slide limiting mechanism such as a slide limiting element that functions to limit the movement of the slide assembly 30 in one of its two linear directions within the inner housing 20*a* in order to limit or restrict the deflection of sheath 90 in one of its deflection directions. As shown in FIGS. 12A, 12B, in some embodiments, the slide limiting element that is used to limit the deflection of the catheter 90 may comprise a slide stop 221*b* that is positioned within the lumen 24 of the inner housing 20*a*. In a specific example, the slide stop 221*b* comprises a tubular slide stop similar to the tubular slide stop 21*b* (shown in FIGS. 2B-2C, 4B-4C, 5A-5D) discussed earlier with reference to FIG. 10D. In some embodiments, as illustrated in FIGS. 12A-12C, the tubular slide stop 221*b* is hollow to accommodate the sheath 90 allowing the sheath 90 to extend to the proximal end of the handle 200. In one embodiment, the tubular slide stop 221*b* comprises a relatively rigid HDPE material. In one example, the tubular slide stop 221*b* has a length [L] of between about 2.15" to about 2.23". In one particular example, the inner diameter (ID) of the slide stop 221*b* ranges from between about 0.25" to about 0.26" and the outer diameter (OD) ranges from between about 0.31" to about 0.32". In a particular example, the slide stop 221*b* has a length that is equal to about 2.19" with inner and outer diameters equal to about 0.255" and 0.315" respectively.

More specifically, with reference again to FIGS. 12A, 12B, in the illustrated embodiment, the slide stop 221*b* is positioned proximal to the slide assembly 30 of the handle 200 and functions to restrict proximal movement of the slide assembly 30 upon actuation of the knob 10 of the handle 100. In some embodiments, the position of the slide stop 221*b* within the inner housing 20*a* may be adjustable. As a result the deflection of the bi-directional steerable sheath or catheter 90 in one of its steering or deflection directions (also referred to as the second deflection direction) is substantially eliminated. However, the distal movement of the slide assembly 30 remains unrestricted. Thus, when the knob 10 is rotated counter-clockwise the slide assembly 30 moves distally within the lumen 24 of the inner housing 20*a*, to allow the slide assembly 30 to pull the control wire 42 to cause a deflection of the steerable sheath or catheter 90 in the other of its two steering or deflection directions (or the first deflection direction). Once the knob 10 is then rotated clock-wise, tension in wire 42 is released until slide assembly 30 returns to its neutral position and the catheter 90 returns to its nominal position. Further clock-wise rotation of the knob results in limited or restricted proximal movement of the slide assembly 30 as it abuts against the tubular slide stop 221b which results in a limited amount of force to be exerted on control wire 40 and the deflection of the catheter in the second deflection direction is substantially eliminated. Therefore the use of a slide limiting element (e.g. slide stop 221b) within handle 200 permits unidirectional use of a bi-directional steering catheter by limiting the proximal movement of the slide assembly to substantially eliminate deflection of the catheter in its second deflection direction, while permitting distal movement of the slide assembly to permit deflection of the catheter in its first deflection direction.

A Unidirectional Control System Using a Slide Limiting Element in Combination with a Slide Assembly Having an Optimized Neutral Position As discussed previously, and presently shown in FIGS. 12A-12C, the curvature of sheath 90 that can be achieved in each of the deflection directions, can also be adjusted by changing the neutral position of the slide assembly 30 in combination with the use of a slide limiting element. The neutral position of the slide assembly is the position where both control wires 40, 42 are in their un-tensioned or relaxed state. As illustrated in FIG. 12B, the slide limiting element (for example, the tubular slide stop 221b) limits the total available translation range [R] of the slide assembly 30 within the lumen 24 along the window 26 of the inner housing 20a. The neutral position of the slide assembly 30 may then be adjusted in order to allocate the range of motion of the slide assembly 30 in each of the proximal and distal directions.

Overview of a Unidirectional Control System with a Slide Assembly Having a Proximal Neutral Position In order to impart unidirectional functionality to a bi-directional steerable catheter of the present invention, the neutral position is set such that the allocated range of motion of the slide assembly in one of the two translation directions is substantially restricted. In the embodiment shown in FIG. 12B, the neutral position [N] is set to be adjacent the proximal boundary of the translation range [R] at a distance [S] from the slide stop 221b, thus substantially restricting the translation of the slide assembly in the proximal direction. In other words, there is limited room for movement of the slide assembly 30 in the proximal direction (as noted by the limited amount of space or distance [S] between the slide assembly 30 and the distal wall 221b' of slide stop 221b). As a result, the deflection of the sheath or catheter 90 in the second deflection direction is substantially eliminated, allowing the handle 200 to impart a unidirectional functionality to the catheter 90 in its first deflection direction allowing it to achieve a first deflected state or position.

Details of the Operation of the Unidirectional Control System Having the Proximal Neutral Position As mentioned previously, during use of the control system or handle 200, when the knob 10 is rotated counter clockwise, the slide assembly 30 moves distally from its neutral position, to tension wire 42 to deflect the catheter 90 in its first deflection direction. As the knob 10 is then rotated clockwise, slide assembly 30 returns to its neutral position and tension is removed from the control wire 42 to allowing the catheter 90 to return close to its un-deflected or nominal shape or state/position. However, resistance observed due to friction between the control wire 42 and the body of the catheter (or sheath) 90 along the length of the catheter 90 prevents the catheter 90 from returning substantially to its un-deflected or nominal shape. A slight curl or bend is still observed in the body of the catheter 90. Thus, there is a need to overcome friction between the control wire 42 and the catheter 90 along the length of the catheter 90 in order to allow the catheter 90 to return to its nominal shape. In order to overcome this friction between the catheter 90 and control wire 42, the opposing control wire 40 is activated by rotating the knob 10 further in the clockwise direction. This allows the slide assembly 30 to travel proximally from its neutral position by distance [S] until it abuts against slide stop 221b, which allows catheter 90 to be uncurled or in other words allows the catheter to return to its un-deflected or nominal state or position by overcoming the force of friction between the control wire 42 and catheter 90. In some embodiments, the distance [S] travelled by the slide assembly 30 to uncurl the catheter 90 (which is equivalent to the neutral position of the slide assembly 30 measured from the slide stop 221b to a proximal wall of the slide assembly 30) is about 2 mm. In some such examples, distance [S] may be range from between about 1.5 mm to about 2.5 mm. Thus, in one particular embodiment, the neutral position of the slide assembly 30 is set such that it is sufficient to allow the catheter to return substantially to its nominal shape or position as the catheter uncurls upon clockwise rotation of the knob 10. However, additional clockwise rotation of the knob 10 is unable to deflect the catheter in its second deflection direction to achieve a second deflected state or position as further movement of the slide assembly is restricted by the slide stop 221b. Therefore, the deflection of the catheter 90 in the second deflection direction is substantially restricted or limited. As such there is no observed deflection of the catheter 90 in the second deflection direction. Thus, the control system or handle 200 of the present invention permits unidirectional use of a bi-directional steerable catheter.

Overview of a Unidirectional Control System with a Slide Assembly Having a Distal Neutral Position and Details of its Operation In some embodiments, as illustrated in FIG. 12C, the slide stop 221b may be utilized, as above, in a position that is proximal to the slide assembly 30. However, unlike the embodiment of FIG. 12B, the slide stop 221b is used to limit the movement of the slide assembly in the opposite direction, i.e. the distal direction to substantially restrict the deflection of the sheath or catheter 90 in its first deflection direction. This may be achieved by altering the neutral position [N] of the slide assembly 30 as illustrated in FIG. 12C. As shown, the neutral position is set to be substantially adjacent to the distal boundary of the translation range [R] at a distance [S] from the distal wall 20a' of the window 26 of the inner housing 20a. The distance [S] is measured from the distal wall 20a' of window 26 to the distal wall of the housing 38 of the slide assembly 30. In one example, the distance [S] is about 2 mm. In some such examples, the distance [S] may range from about 1.5 mm to about 2.5 mm. This neutral position [N] substantially restricts the translation of the slide assembly in the distal direction upon counter-clockwise rotation of the knob 10. As a result minimal force is exerted on the control wire 42 such that deflection of the catheter 90 in the first deflection direction is substantially eliminated.

As an overview of the operation of the illustrated embodiment of FIG. 12C, starting from its neutral position [N] the slide assembly 30 is free to translate proximally within the handle 200 upon clockwise rotation of the knob, until the slide assembly 30 abuts against the distal wall 221b' of the slide stop 221b. This allowing force to be exerted on control wire 40 deflecting catheter 90 in its second deflection direction, thus imparting unidirectional functionality to the bi-directional steerable catheter 90. The inner knob 10a may then be rotated counter-clockwise until tension is removed from control wire 40 and the slide assembly 30 returns to its nominal position [N]. Similar to the embodiment discussed previously, the catheter 90 may be deflected close to its nominal shape but friction between the control wire 40 and the catheter 90 along the length of the catheter 90 may prevent the catheter 90 from returning completely to its nominal shape and a slight curl or bend may remain in the catheter 90. As the knob 10 is then rotated further counter-clockwise the slide assembly 30 moves distally until it abuts against the proximal wall 20a' of the window 26 of the inner housing 20a (which prevents it from travelling further distally) which allows the catheter to return substantially to its nominal position or shape but prevents the catheter 90 from deflecting substantially in its first deflection direction.

A Unidirectional Control System Using a Slide Limiting Element Positioned Distal to the Slide Assembly Alternatively, the slide limiting element may be positioned distal to the slide assembly 30 in order to permit unidirectional use of the bi-directional steering catheter by substantially restricting the distal movement of the slide assembly. In one such example, the slide limiting element may be positioned distal to the carriage 34 of the slide assembly 30 (similar to collar 21y illustrated in FIG. 10e). The collar substantially restricts the distal movement of the slide assembly 30 upon counter clockwise rotation of the knob, in order to substantially eliminate deflection of the sheath or catheter 90 in its first deflection direction. However, the slide assembly 30 is free to move proximally within the handle upon clockwise rotation of the knob in order to pull control wire 40 to cause deflection of the catheter in its second deflection direction. Thus, the slide limiting element may alternatively be used to permits unidirectional use of a bi-directional steering catheter by limiting the movement of the slide assembly to substantially eliminate deflection of the catheter in its first deflection direction while permitting deflection in its second deflection direction. In some embodiments, the collar 21y may be positioned to permit limited distal movement of the slide assembly 30 to permit straightening or uncurling of the catheter after it has been deflected in its second deflection direction.

Unidirectional Control System Using Alternative Embodiments of a Slide Limiting Element As an alternative, any of the slide limiting elements discussed herein above in FIGS. 10a-10h may be used to substantially restrict the translation of the slide assembly in one of its linear translation directions to permit unidirectional use of the bi-directional steerable catheter.

Thus, as described hereinabove, embodiments of the present invention provide a rotatable mechanism for controlling deflection of two control or pull wires using one moving member to allow a catheter or other medical device to be steered in two different directions. The rotation of the knob in a first rotational direction moves the member along one longitudinal direction to allow one of the two control wires to be placed in tension (to deflect the catheter to a first orientation) and rotation of the knob in an opposite rotational direction (about a longitudinal axis of the handle) moves the member along the opposite longitudinal direction to allow the other of the two control wires to be placed in tension (to deflect the catheter to a different orientation).

In one broad aspect, embodiments of the present invention provide a control system for bi-directional control of a steerable catheter, the catheter including at least two control wires, a distal end of each of the control wires being coupled to the catheter at a distal region thereof, the control system comprising: a housing coupled to the catheter; a slide assembly positioned within the housing and operable to translate linearly therein; a proximal portion of each of the at least two control wires being mounted or positioned through the slide assembly; and a control knob rotatably coupled to the housing for linearly translating the slide assembly, thereby enabling the slide assembly to separately manipulate each of said at least two control wires to effect a change in a deflection of said catheter; wherein rotation of the control knob in a first rotational direction causes distal movement of the slide assembly in a first linear direction causing the slide assembly to tension one of said at least two control wires thereby effecting a change in the deflection of said catheter in a first deflection direction and wherein rotation of the knob in a second rotational direction causes proximal movement of the slide assembly in a second linear direction causing the slide assembly to tension the other of said at least two control wires thereby effecting a change in the deflection of said catheter in a second deflection direction.

In another broad aspect, embodiments of the present invention provide a slack limiting or containing device for use with a steerable catheter control system having at least one control wire, the control system comprising a mechanism for tensioning the at least one control wire for deflecting the steerable catheter and for releasing tension there-from, wherein the slack limiting device is engageable with a portion of the at least one control wire for limiting the slack therein when tension is released from the at least one control wire.

In yet another broad aspect, embodiments of the present invention provide a slack limiting device for use with a steerable catheter control system having at least one control wire, the control system comprising a mechanism for tensioning the at least one control wire for deflecting the steerable catheter and for releasing tension there-from, wherein the slack limiting device is engageable with a portion of the at least one control wire for limiting the slack therein when tension is released from the at least one control wire.

In a further broad aspect, embodiments of the present invention provide a slide limiting or restricting mechanism for use with a steerable control system for a steerable catheter having at least one control wire, the steerable control system comprising a handle having a housing with a single slide assembly disposed within the housing that has the at least one control wire coupled thereto, and a rotatable knob for moving the single slide assembly to cause a deflection of the catheter by tensioning the at least one control wire, the slide limiting mechanism comprising: a slide limiting or restricting element positioned within the handle to limit a linear movement of the single slide assembly in a first linear direction within the handle upon rotation of the knob in a first rotational direction, to limit the tension placed on the at least one control wire, for limiting the deflection of the catheter in a first deflection direction.

In an additional broad aspect, embodiments of the present invention provide a method for using a control system to deflect a steerable catheter, the control system comprising a handle having a housing and a single slide assembly disposed within the housing that is operable via a knob, the steerable catheter comprising at least two control wires that are passed through the single slide assembly for engaging therewith, for steering the catheter in opposite deflection directions, the method comprising: moving the single slide assembly in a first linear direction to place one of the at least two control wires in tension by rotating the knob in a first rotational direction, in order to deflect the catheter in a first deflection direction; and moving the single slide assembly in a second linear direction opposite to the first linear direction to place the other of the at least two control wires in tension by rotating the knob in a second rotational direction, in order to deflect the catheter in a second deflection direction.

In still an additional broad aspect, embodiments of the present invention provide a control system for providing unidirectional control of a bi-directional steerable catheter having at least two deflection directions, the control system comprising an actuator for permitting deflection of the bi-directional steerable catheter in a first deflection direction upon actuation in a first direction and comprising a deflection limiting mechanism for substantially limiting the deflection of the bi-directional steerable catheter in a second deflection direction by limiting actuation in a second direction.

As a features of these broad aspects, embodiments of the present invention provide a handle which includes a rotatable mechanism for controlling tension of two pull wires. Rotation of the mechanism in one direction tensions and thus applies a pulling force on a first pull wire, whereas rotation in the opposite direction tensions and thus applies a pulling force on the second pull wire. As is further described herein, such tensioning of the wires can be used to torque or deflect a functional end of a medical device connected to the handle.

Some such embodiments comprise a handle for bi-directional control of a catheter, the handle comprising: a housing; a control knob rotatably coupled to the housing for co-operatively engaging with a slide positioned within said housing; a first control wire and a second control wire, a proximal end of each of said control wires being coupled to the slide and a distal end of each of said control wires being coupled to the catheter; wherein rotation of the knob causes the slide to translate linearly within said housing to change the tension in one of said first and second control wires to effect a change in the deflection of said catheter.

As another feature of these embodiments, the slide comprises at least three openings/passages extending longitudinally at least partially through the slide to allow said first and second control wires to be passed there-through to be coupled thereto.

In a further example of this feature, the at least three openings/passages comprise: a first opening and a second opening, allowing the first and the second control wires to pass proximally there-through, the first control wire being coupled to a proximal face of said slide, a third opening allowing the second control wire to additionally pass distally there-through via a pulley to be coupled to distal face of the slide.

In another example of this feature, the slide defines a hollow interior between a slide distal end defining said distal face and a slide proximal end defining said proximal face, to allow free passage for/to prevent strain on said first and second control wires.

In still a further example of this feature, said first and third openings/passages housing said second control wire are positioned towards the exterior of the slide to prevent stress on the second control wire and to prevent the slide from rotating within the housing.

As an additional feature of this broad aspect, the slide comprises a cap and a base. In an example of this feature, the cap comprises teeth that co-operatively engage with grooves within the slide to form said at least three openings. In a further example of this feature, the slide further comprises a central opening to allow the first and second control wires to pass there-through to allow the wires to be routed through the grooves within the slide. In a particular example of this the central opening is in the form of a groove within the base.

As still an additional feature of this broad aspect, the handle comprises a slack limiting/containing element for limiting/containing slack in at least one of the first and second control wires.

As a further feature of this broad aspect, the handle further comprises a means for coupling the pull wires to opposite sides of the slide so that motion of the slide in one direction will apply tension to one wire while motion of the slide in the other direction will apply tension to the other wire. In one particular example, one of said first and second control wires are coupled to the slide through/via a pulley. In an example of this feature, the handle comprises a pulley guide to maintain engagement of the second control wire with said pulley. In an additional example of this feature, the handle comprises a height guide to maintain engagement of the second control wire with said pulley.

As still an additional feature of this broad aspect, the handle further comprises a groove extending longitudinally within the housing for receiving a projection within the slide to guide the slide within the housing.

As still an additional feature of this broad aspect, the handle comprises a resistance/frictional element within the inner knob and the outer knob to maintain a position of the slider to maintain a curve/deflection of the catheter. In a further example of this feature the resistance/frictional element comprises an o-ring.

As another feature of this broad aspect, the inner housing comprises a slide limiting element to limit the translation of the slide within the housing to limit the tension placed on at least one of said first and second control wires.

As a feature of this broad aspect, the slide limiting element is adjustable. In an example of this feature, wherein an initial position of the slide is variable.

In a further broad aspect, embodiments of the present invention comprise a steerable catheter having one or more control wires comprising a slack limiting/containing element for limiting/containing slack in at least one of the one or more control wires.

As a feature of this aspect, the slack limiting/containing element comprises a friction element.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A control system for bi-directional control of a steerable catheter, the catheter including at least two control wires, a distal end of each of the control wires being coupled to the catheter at a distal region thereof, the control system comprising:
   a housing coupled to the catheter, the housing defining a lumen;
   a slide assembly positioned within the lumen of the housing and operable to translate linearly therein, the housing defining an inner wall configured to guide the slide assembly to enable linear translation of the slide assembly within the lumen of the housing;
   a proximal portion of each of the at least two control wires being positioned through the slide assembly; and
   a control knob rotatably coupled to the housing, for linearly translating the slide assembly, thereby enabling the slide assembly to separately manipulate each of said at least two control wires to effect a change in a deflection of said catheter;
   wherein the control knob is coupled to the housing in a rotatable but non-translational relationship and wherein rotation of the control knob in a first rotational direction causes distal movement of the slide assembly in a first linear direction causing the slide assembly to tension one of said at least two control wires thereby effecting a change in the deflection of said catheter in a first deflection direction and wherein rotation of the knob in a second rotational direction causes proximal movement of the slide assembly in a second linear direction causing the slide assembly to tension the other of said at least two control wires thereby effecting a change in the deflection of said catheter in a second deflection direction;
   wherein one of said at least two control wires is indirectly coupled to the slide assembly via a direction reversing element and wherein the direction reversing element is substantially in plane with the at least two control wires;
   wherein the slide assembly is substantially centrally positioned within the lumen defined by the housing;
   wherein the slide assembly comprises a first component, the first component comprising a sliding component for slidably engaging a portion of the housing, and said slide assembly further comprises a second component, the second component comprising a threaded component for engaging with the control knob; and
   wherein the threaded component is receivable within the control knob to be threadably engaged thereto along a longitudinal axis thereof.

2. The control system of claim 1 further comprising a slide limiting element positioned within the housing for limiting linear translation of the slide assembly within the housing to limit allowable deflection of the catheter.

3. The control system of claim 2, wherein the slide limiting element comprises a tubular slide stop.

4. The control system of claim 2, wherein the slide limiting element is positioned proximal to the slide assembly.

5. The control system of claim 2, wherein the slide limiting element is adjustable for altering the allowable deflection of the catheter in one or more of the first and second deflection directions.

6. The control system of claim 2, wherein a neutral position of the slide assembly is adjustable in combination with the slide limiting element for altering the allowable deflection of the catheter in one or more of the first and second deflection directions.

7. The control system of claim 1, further comprising a slack limiting element for limiting slack in one of the at least two control wires.

8. The control system of claim 7, wherein the slack limiting element comprises a friction device for frictionally engaging the one of the at least two control wires for limiting slack therein.

9. The control system of claim 8, wherein the friction device comprises vertically extending pins defining gaps there-between for receiving the other of the at least two control wires.

10. The control system of claim 1, wherein the direction reversing element is positioned at a proximal region of the control system.

11. The control system of claim 1, wherein the direction reversing element comprises a pulley.

12. The control system of claim 11, further comprising a pulley guide substantially adjacent to and surrounding at least a portion of the pulley for positioning the one of the at least two control wires there-through.

13. The control system of claim 11, further comprising a vertical guide for maintaining a position of the one of the at least two control wires along a vertical plane of the pulley to assist in retaining the one of the at least two control wires about the pulley.

14. The control system of claim 1, wherein the knob is rotatable about a longitudinal axis of the control system.

15. The control system of claim 14, wherein the knob is threadably engaged with the slide assembly.

16. The control system of claim 15, wherein the slide assembly comprises a discontinuous thread.

17. The control system of claim 14 further comprising a position maintaining element to maintain a position of the knob relative to the housing upon rotation of the knob to maintain the deflection of the catheter in one of the first or second deflection directions.

18. The control system of claim 17, wherein the position maintaining element comprises a resistance element located at an interface between the knob and the housing for creating friction there-between.

19. The control system of claim 1 wherein the slide assembly comprises a carriage comprising:
   a base defining at least three grooves for receiving said at least two control wires; and
   a cap for retaining said at least two control wires within said at least three grooves;
   wherein said cap co-operatively engages with said grooves to define at least three passages.

20. The control system of claim 19, wherein said at least two control wires comprise a first control wire and a second control wire and wherein the first control wire is positioned within a first of the at least three passages such that a proximal end of the first control wire is located proximally of the slide assembly, and wherein the second control wire is positioned within a third of the at least three passages, the second control wire through a second of the at least three passages such that a proximal end of the second control wire is located distally of the slide assembly wherein the first and third passages are positioned towards opposing lateral edges of the slide assembly for minimizing strain in the second control wire.

21. The control system of claim 1, wherein the inner wall of the housing defines a track for receiving a portion of the slide assembly for preventing rotation of the slide assembly.

22. The control system of claim 1, wherein the inner wall of the housing defines at least one substantially planar inner surface for interacting with the slide assembly to prevent rotation thereof upon rotation of the control knob to facilitate linear movement of the slide assembly within the housing.

23. The control system of claim 22, wherein the slide assembly comprises at least one substantially planar outer surface for interacting with said at least one planar inner surface of the housing to prevent rotation of the slide assembly.

24. The control system of claim 23, wherein an inner width of the housing is substantially equal to a width of the slide assembly to permit linear movement of the slide assembly in sliding engagement therewith.

25. The control system of claim 22, wherein the at least one substantially planar inner surface comprises two laterally opposed substantially planar inner surfaces.

26. The control system of claim 1, wherein the sliding component comprising an intermediate housing comprising a carriage.

27. The control system of claim 1, wherein the threaded component is integral with the sliding component.

28. The control system of claim 1, wherein the threaded component is distal of the sliding component.

29. A method of using a control system for deflecting a steerable catheter, the control system comprising a handle having a housing defining a lumen and a single slide assembly disposed within the lumen of the housing, that is operable via a knob coupled to the housing, the housing defining an inner wall of the housing configured to guide the slide assembly to enable linear translation of the slide assembly within the lumen, the steerable catheter comprising at least two control wires that are passed through the single slide assembly for engaging therewith for steering the catheter in opposite deflection directions, the method comprising:
    moving the single slide assembly along the inner wall of the housing in a first linear direction to place one of the at least two control wires in tension by rotating the knob in a first rotational direction, in order to deflect the catheter in a first deflection direction; and
    moving the single slide assembly along the inner wall of the housing in a second linear direction opposite to the first linear direction to place the other of the at least two control wires in tension by rotating the knob in a second rotational direction, in order to deflect the catheter in a second deflection direction wherein the interaction between the single slide assembly and the inner wall of the housing prevents rotational movement of the slide assembly while permitting linear translation thereof within the housing;
    wherein one of the at least two control wires being indirectly coupled to the slide assembly via a direction reversing element that is substantially in plane with the at least two control wires, wherein a force required to place each of the two control wires in tension is substantially similar;
    wherein the slide assembly is substantially centrally positioned within the lumen defined by the housing;
    wherein the slide assembly comprises a first component, the first component comprising a sliding component for slidably engaging a portion of the housing, and said slide assembly further comprises a second component, the second component comprising a threaded component for engaging with the control knob; and
    wherein the threaded component is receivable within the control knob to be threadably engaged thereto along a longitudinal axis thereof.

\* \* \* \* \*